(12) United States Patent
Yu et al.

(10) Patent No.: US 12,319,958 B2
(45) Date of Patent: Jun. 3, 2025

(54) METHOD AND KIT FOR CCR2 EXPRESSION PROFILING AND DISEASE STRATIFICATION

(71) Applicants: Rutgers, The State University of New Jersey, New Brunswick, NJ (US); Plumeria Therapeutics, Inc., Plainsboro, NJ (US)

(72) Inventors: Lei Yu, Belle Mead, NJ (US); Thomas P. Richardson, West Windsor, NJ (US)

(73) Assignees: Rutgers, The State University of New Jersey, New Brunswick, NJ (US); Plumeria Therapeutics, Inc., Plainsboro, NJ (US)

(*) Notice: Subject to any disclaimer, the term of this patent is extended or adjusted under 35 U.S.C. 154(b) by 82 days.

(21) Appl. No.: 17/382,240

(22) Filed: Jul. 21, 2021

(65) Prior Publication Data

US 2022/0025436 A1   Jan. 27, 2022

Related U.S. Application Data

(60) Provisional application No. 63/054,407, filed on Jul. 21, 2020.

(51) Int. Cl.
  *C12Q 1/68* (2018.01)
  *C12Q 1/6851* (2018.01)
  *C12Q 1/686* (2018.01)

(52) U.S. Cl.
  CPC ........... *C12Q 1/686* (2013.01); *C12Q 1/6851* (2013.01)

(58) Field of Classification Search
  None
  See application file for complete search history.

(56) References Cited

U.S. PATENT DOCUMENTS

| | | | | |
|---|---|---|---|---|
| 6,600,030 | B2* | 7/2003 | Dean | C07K 14/7158 435/71.1 |
| 8,710,191 | B2* | 4/2014 | Gladue | A61P 31/20 530/388.22 |
| 2017/0348442 | A1* | 12/2017 | Liu | A61K 51/08 |
| 2021/0317461 | A1* | 10/2021 | Novobrantseva | A61K 45/06 |

FOREIGN PATENT DOCUMENTS

WO   2010071567 A1   6/2010

OTHER PUBLICATIONS

Tanaka et al. (Biochem Biophys Res Comm, 2002, 290:73-80) (Year: 2002).*

(Continued)

*Primary Examiner* — Stephanie K Mummert
(74) *Attorney, Agent, or Firm* — Hamilton, Brook, Smith & Reynolds, P.C.

(57) ABSTRACT

Methods of treating disease include measuring a CCR2 profile of a patent, selecting a CCR2 antagonist based on the CCR2 profile of the patient, and administering the CCR2 antagonist to the patient. Methods for stratifying one or more patients for pain medication based on a CCR2 profile include measuring a CCR2 profile of one or more patients and partitioning the one or more patients into predetermined groups or subgroups based on the CCR2 profile of the one or more patients. Kits for performing the methods are also described.

20 Claims, 20 Drawing Sheets
Specification includes a Sequence Listing.

(56) References Cited

OTHER PUBLICATIONS

Mirzadegan et al. (J of Biol Chem, 2000, 275(33):25562-25571) (Year: 2000).*
Lowe et al. (Nucleic Acids Research, 1990, 18(7):1757-1761) (Year: 1990).*
Wong et al. (Journal of Biol Chem, 1997, 272(2):1038-1045) (Year: 1997).*
Zavrsnik (Zavrnik M. Polymorphisms of inflammatory genes . . . of diabetic nephropathy in patients with type 2 diabetes. Dissertation, Univ. of Zagreb, School of Medicine, 2018) (Year: 2018).*
Soltys et al. (2021, Aresty Rutgers Undergraduate Research Journal, vol. 1, issue III, p. 1-4) (Year: 2021).*

* cited by examiner

Human CCR2 Receptor Isoform A vs B Protein Sequence Comparison

```
Human_CCR2-A    1 MLSTSRSRFIRNTNESGEEVTTFFDYDYGAPCHKFDVKQIGAQLLPPLYS   50
                  ||||||||||||||||||||||||||||||||||||||||||||||||||
Human_CCR2-B    1 MLSTSRSRFIRNTNESGEEVTTFFDYDYGAPCHKFDVKQIGAQLLPPLYS   50

Human_CCR2-A   51 LVFIFGFVGNMLVVLILINCKKLKCLTDIYLLNLAISDLLFLITLPLWAH  100
                  ||||||||||||||||||||||||||||||||||||||||||||||||||
Human_CCR2-B   51 LVFIFGFVGNMLVVLILINCKKLKCLTDIYLLNLAISDLLFLITLPLWAH  100

Human_CCR2-A  101 SAANEWVFGNAMCKLFTGLYHIGYFGGIFFIILLTIDRYLAIVHAVFALK  150
                  ||||||||||||||||||||||||||||||||||||||||||||||||||
Human_CCR2-B  101 SAANEWVFGNAMCKLFTGLYHIGYFGGIFFIILLTIDRYLAIVHAVFALK  150

Human_CCR2-A  151 ARTVTFGVVTSVITWLVAVFASVPGIIFTKCQKEDSVYVCGPYFPRGWNN  200
                  ||||||||||||||||||||||||||||||||||||||||||||||||||
Human_CCR2-B  151 ARTVTFGVVTSVITWLVAVFASVPGIIFTKCQKEDSVYVCGPYFPRGWNN  200

Human_CCR2-A  201 FHTIMRNILGLVLPLLIMVICYSGILKTLLRCRNEKKRHRAVRVIFTIMI  250
                  ||||||||||||||||||||||||||||||||||||||||||||||||||
Human_CCR2-B  201 FHTIMRNILGLVLPLLIMVICYSGILKTLLRCRNEKKRHRAVRVIFTIMI  250

Human_CCR2-A  251 VYFLFWTPYNIVILLNTFQEFFGLSNCESTSQLDQATQVTETLGMTHCCI  300
                  ||||||||||||||||||||||||||||||||||||||||||||||||||
Human_CCR2-B  251 VYFLFWTPYNIVILLNTFQEFFGLSNCESTSQLDQATQVTETLGMTHCCI  300

Human_CCR2-A  301 NPIIYAFVGEKFRSLFHIALGCRIAPLQKPVCGGPGVRPGKNVKVTTQGL  350
                  |||||||||||||    |         |         |    |    |
Human_CCR2-B  301 NPIIYAFVGEKFRRYLSVFFRKHITKRFCKQCPVFYRETVDGVTSTNTPS  350

Human_CCR2-A  351 LDGRGKGKSIGRAPEASLQDKEGA                           374

Human_CCR2-B  351 TGEQEVSAGL                                         360
```

FIG. 1

| | | | |
|---|---|---|---|
| Human_CCR2A | 1 | TTTATTCTCTGGAACATGAAACATTCTGTTGTGCTCATATCATGCAAATT | 50 |
| Human_CCR2B | 1 | TTTATTCTCTGGAACATGAAACATTCTGTTGTGCTCATATCATGCAAATT | 50 |
| Human_CCR2A | 51 | ATCACTAGTAGGAGAGCAGAGAGTGGAAATGTTCCAGGTATAAAGACCCA | 100 |
| Human_CCR2B | 51 | ATCACTAGTAGGAGAGCAGAGAGTGGAAATGTTCCAGGTATAAAGACCCA | 100 |
| Human_CCR2A | 101 | CAAGATAAAGAAGCTCAGAGTCGTTAGAAACAGGAGCAGATGTACAGGGT | 150 |
| Human_CCR2B | 101 | CAAGATAAAGAAGCTCAGAGTCGTTAGAAACAGGAGCAGATGTACAGGGT | 150 |
| Human_CCR2A | 151 | TTGCCTGACTCACACTCAAGGTTGCATAAGCAAGATTTCAAAATTAATCC | 200 |
| Human_CCR2B | 151 | TTGCCTGACTCACACTCAAGGTTGCATAAGCAAGATTTCAAAATTAATCC | 200 |
| Human_CCR2A | 201 | TATTCTGGAGACCTCAACCCAATGTACAATGTTCCTGACTGGAAAAGAAG | 250 |
| Human_CCR2B | 201 | TATTCTGGAGACCTCAACCCAATGTACAATGTTCCTGACTGGAAAAGAAG | 250 |
| Human_CCR2A | 251 | AACTATATTTTTCTGATTTTTTTTTTCAAATCTTTACCATTAGTTGCCCT | 300 |
| Human_CCR2B | 251 | AACTATATTTTTCTGATTTTTTTTTTCAAATCTTTACCATTAGTTGCCCT | 300 |
| Human_CCR2A | 301 | GTATCTCCGCCTTCACTTTCTGCAGGAAACTTTATTTCCTACTTCTGCAT | 350 |
| Human_CCR2B | 301 | GTATCTCCGCCTTCACTTTCTGCAGGAAACTTTATTTCCTACTTCTGCAT | 350 |
| Human_CCR2A | 351 | GCCAAGTTTCTACCTCTAGATCTGTTTGGTTCAGTTGCTGAGAAGCCTGA | 400 |
| Human_CCR2B | 351 | GCCAAGTTTCTACCTCTAGATCTGTTTGGTTCAGTTGCTGAGAAGCCTGA | 400 |
| Human_CCR2A | 401 | CATACCAGGACTGCCTGAGACAAGCCACAAGCTGAACAGAGAAAGTGGAT | 450 |
| Human_CCR2B | 401 | CATACCAGGACTGCCTGAGACAAGCCACAAGCTGAACAGAGAAAGTGGAT | 450 |
| Human_CCR2A | 451 | TGAACAAGGACGCATTTCCCCAGTACATCCACAACATGCTGTCCACATCT | 500 |
| Human_CCR2B | 451 | TGAACAAGGACGCATTTCCCCAGTACATCCACAACATGCTGTCCACATCT | 500 |
| Human_CCR2A | 501 | CGTTCTCGGTTTATCAGAAATACCAACGAGAGCGGTGAAGAAGTCACCAC | 550 |
| Human_CCR2B | 501 | CGTTCTCGGTTTATCAGAAATACCAACGAGAGCGGTGAAGAAGTCACCAC | 550 |

FIG. 2

```
Human_CCR2A   551 CTTTTTTGATTATGATTACGGTGCTCCCTGTCATAAATTTGACGTGAAGC  600
                  ||||||||||||||||||||||||||||||||||||||||||||||||||
Human_CCR2B   551 CTTTTTTGATTATGATTACGGTGCTCCCTGTCATAAATTTGACGTGAAGC  600

Human_CCR2A   601 AAATTGGGGCCCAACTCCTGCCTCCGCTCTACTCGCTGGTGTTCATCTTT  650
                  ||||||||||||||||||||||||||||||||||||||||||||||||||
Human_CCR2B   601 AAATTGGGGCCCAACTCCTGCCTCCGCTCTACTCGCTGGTGTTCATCTTT  650

Human_CCR2A   651 GGTTTTGTGGGCAACATGCTGGTCGTCCTCATCTTAATAAACTGCAAAAA  700
                  ||||||||||||||||||||||||||||||||||||||||||||||||||
Human_CCR2B   651 GGTTTTGTGGGCAACATGCTGGTCGTCCTCATCTTAATAAACTGCAAAAA  700

Human_CCR2A   701 GCTGAAGTGCTTGACTGACATTTACCTGCTCAACCTGGCCATCTCTGATC  750
                  ||||||||||||||||||||||||||||||||||||||||||||||||||
Human_CCR2B   701 GCTGAAGTGCTTGACTGACATTTACCTGCTCAACCTGGCCATCTCTGATC  750

Human_CCR2A   751 TGCTTTTTCTTATTACTCTCCCATTGTGGGCTCACTCTGCTGCAAATGAG  800
                  ||||||||||||||||||||||||||||||||||||||||||||||||||
Human_CCR2B   751 TGCTTTTTCTTATTACTCTCCCATTGTGGGCTCACTCTGCTGCAAATGAG  800

Human_CCR2A   801 TGGGTCTTTGGGAATGCAATGTGCAAATTATTCACAGGGCTGTATCACAT  850
                  ||||||||||||||||||||||||||||||||||||||||||||||||||
Human_CCR2B   801 TGGGTCTTTGGGAATGCAATGTGCAAATTATTCACAGGGCTGTATCACAT  850

Human_CCR2A   851 CGGTTATTTTGGCGGAATCTTCTTCATCATCCTCCTGACAATCGATAGAT  900
                  ||||||||||||||||||||||||||||||||||||||||||||||||||
Human_CCR2B   851 CGGTTATTTTGGCGGAATCTTCTTCATCATCCTCCTGACAATCGATAGAT  900

Human_CCR2A   901 ACCTGGCTATTGTCCATGCTGTGTTTGCTTTAAAAGCCAGGACGGTCACC  950
                  ||||||||||||||||||||||||||||||||||||||||||||||||||
Human_CCR2B   901 ACCTGGCTATTGTCCATGCTGTGTTTGCTTTAAAAGCCAGGACGGTCACC  950

Human_CCR2A   951 TTTGGGGTGGTGACAAGTGTGATCACCTGGTTGGTGGCTGTGTTTGCTTC  1000
                  ||||||||||||||||||||||||||||||||||||||||||||||||||
Human_CCR2B   951 TTTGGGGTGGTGACAAGTGTGATCACCTGGTTGGTGGCTGTGTTTGCTTC  1000

Human_CCR2A  1001 TGTCCCAGGAATCATCTTTACTAAATGCCAGAAAGAAGATTCTGTTTATG  1050
                  ||||||||||||||||||||||||||||||||||||||||||||||||||
Human_CCR2B  1001 TGTCCCAGGAATCATCTTTACTAAATGCCAGAAAGAAGATTCTGTTTATG  1050

Human_CCR2A  1051 TCTGTGGCCCTTATTTTCCACGAGGATGGAATAATTTCCACACAATAATG  1100
                  ||||||||||||||||||||||||||||||||||||||||||||||||||
Human_CCR2B  1051 TCTGTGGCCCTTATTTTCCACGAGGATGGAATAATTTCCACACAATAATG  1100
```

FIG. 2 (Continued)

```
Human_CCR2A   1101 AGGAACATTTTGGGGCTGGTCCTGCCGCTGCTCATCATGGTCATCTGCTA 1150
                   ||||||||||||||||||||||||||||||||||||||||||||||||||
Human_CCR2B   1101 AGGAACATTTTGGGGCTGGTCCTGCCGCTGCTCATCATGGTCATCTGCTA 1150

Human_CCR2A   1151 CTCGGGAATCCTGAAAACCCTGCTTCGGTGTCGAAACGAGAAGAAGAGGC 1200
                   ||||||||||||||||||||||||||||||||||||||||||||||||||
Human_CCR2B   1151 CTCGGGAATCCTGAAAACCCTGCTTCGGTGTCGAAACGAGAAGAAGAGGC 1200

Human_CCR2A   1201 ATAGGGCAGTGAGAGTCATCTTCACCATCATGATTGTTTACTTTCTCTTC 1250
                   ||||||||||||||||||||||||||||||||||||||||||||||||||
Human_CCR2B   1201 ATAGGGCAGTGAGAGTCATCTTCACCATCATGATTGTTTACTTTCTCTTC 1250

Human_CCR2A   1251 TGGACTCCCTATAATATTGTCATTCTCCTGAACACCTTCCAGGAATTCTT 1300
                   ||||||||||||||||||||||||||||||||||||||||||||||||||
Human_CCR2B   1251 TGGACTCCCTATAATATTGTCATTCTCCTGAACACCTTCCAGGAATTCTT 1300

Human_CCR2A   1301 CGGCCTGAGTAACTGTGAAAGCACCAGTCAACTGGACCAAGCCACGCAGG 1350
                   ||||||||||||||||||||||||||||||||||||||||||||||||||
Human_CCR2B   1301 CGGCCTGAGTAACTGTGAAAGCACCAGTCAACTGGACCAAGCCACGCAGG 1350

Human_CCR2A   1351 TGACAGAGACTCTTGGGATGACTCACTGCTGCATCAATCCCATCATCTAT 1400
                   ||||||||||||||||||||||||||||||||||||||||||||||||||
Human_CCR2B   1351 TGACAGAGACTCTTGGGATGACTCACTGCTGCATCAATCCCATCATCTAT 1400

Human_CCR2A   1401 GCCTTCGTTGGGGAGAAGTTCAGA-------------------------- 1424
                   ||||||||||||||||||||||||
Human_CCR2B   1401 GCCTTCGTTGGGGAGAAGTTCAGAAGGTATCTCTCGGTGTTCTTCCGAAA 1450

Human_CCR2A   1425 -------------------------------------------------- 1424
Human_CCR2B   1451 GCACATCACCAAGCGCTTCTGCAAACAATGTCCAGTTTTCTACAGGGAGA 1500

Human_CCR2A   1425 -------------------------------------------------- 1424
Human_CCR2B   1501 CAGTGGATGGAGTGACTTCAACAAACACGCCTTCCACTGGGGAGCAGGAA 1550

Human_CCR2A   1425 -------------------------------------------------- 1424
Human_CCR2B   1551 GTCTCGGCTGGTTTATAAAACGAGGAGCAGTTTGATTGTTGTTTATAAAG 1600

Human_CCR2A   1425 -------------------------------------------------- 1424
Human_CCR2B   1601 GGAGATAACAATCTGTATATAACAACAAACTTCAAGGGTTTGTTGAACAA 1650
```

FIG. 2 (Continued)

```
Human_CCR2A    1425 ----------------------------------------------------  1424
Human_CCR2B    1651 TAGAAACCTGTAAAGCAGGTGCCCAGGAACCTCAGGGCTGTGTGTACTAA    1700

Human_CCR2A    1425 ----------------------------------------------------  1424
Human_CCR2B    1701 TACAGACTATGTCACCCAATGCATATCCAACATGTGCTCAGGGAATAATC    1750

Human_CCR2A    1425 ----------------------------------------------------  1424
Human_CCR2B    1751 CAGAAAAACTGTGGGTAGAGACTTTGACTCTCCAGAAAGCTCATCTCAGC    1800

Human_CCR2A    1425 ----------------------------------------------------  1424
Human_CCR2B    1801 TCCTGAAAAATGCCTCATTACCTTGTGCTAATCCTCTTTTTCTAGTCTTC    1850

Human_CCR2A    1425 ----------------------------------------------------  1424
Human_CCR2B    1851 ATAATTTCTTCACTCAATCTCTGATTCTGTCAATGTCTTGAAATCAAGGG    1900

Human_CCR2A    1425 ----------------------------------------------------  1424
Human_CCR2B    1901 CCAGCTGGAGGTGAAGAAGAGAATGTGACAGGCACAGATGAATGGGAGTG    1950

Human_CCR2A    1425 ----------------------------------------------------  1424
Human_CCR2B    1951 AGGGATAGTGGGGTCAGGGCTGAGAGGAGAAGGAGGGAGACATGAGCATG    2000

Human_CCR2A    1425 ----------------------------------------------------  1424
Human_CCR2B    2001 GCTGAGCCTGGACAAAGACAAAGGTGAGCAAAGGGCTCACGCATTCAGCC    2050

Human_CCR2A    1425 ----------------------------------------------------  1424
Human_CCR2B    2051 AGGAGATGATACTGGTCCTTAGCCCCATCTGCCACGTGTATTTAACCTTG    2100

Human_CCR2A    1425 ----------------------------------------------------  1424
Human_CCR2B    2101 AAGGGTTCACCAGGTCAGGGAGAGTTTGGGAACTGCAATAACCTGGGAGT    2150

Human_CCR2A    1425 ----------------------------------------------------  1424
Human_CCR2B    2151 TTTGGTGGAGTCCGATGATTCTCTTTTGCATAAGTGCATGACATATTTTT    2200
```

FIG. 2 (Continued)

| | | |
|---|---|---|
| Human_CCR2A | 1425 ---------------------------------------------- | 1424 |
| Human_CCR2B | 2201 GCTTTATTACAGTTTATCTATGGCACCCATGCACCTTACATTTGAAATCT | 2250 |
| Human_CCR2A | 1425 ---------------------------------------------- | 1424 |
| Human_CCR2B | 2251 ATGAAATATCATGCTCCATTGTTCAGATGCTTCTTAGGCCACATCCCCCT | 2300 |
| Human_CCR2A | 1425 ---------------------------------------------- | 1424 |
| Human_CCR2B | 2301 GTCTAAAAATTCAGAAAATTTTTGTTTATAAAAGATGCATTATCTATGAT | 2350 |
| Human_CCR2A | 1425 ---------------------------------------------- | 1424 |
| Human_CCR2B | 2351 ATGCTAATATATGTATATGCAATATATATAGGCTCTTGCTTGATCTCTCC | 2400 |
| Human_CCR2A | 1425 ---------------------------------------------- | 1424 |
| Human_CCR2B | 2401 AGGAGGTAGTGATTATGAGAAGGGGGTGGAGAATGATGAGTTCCTTCACC | 2450 |
| Human_CCR2A | 1425 ---------------------------------------------- | 1424 |
| Human_CCR2B | 2451 AGGAGCAAAGGACGGGGATCGTGTGGAACCACTGCAGAACTATTTCCGAA | 2500 |
| Human_CCR2A | 1425 ---------------------------------------------- | 1424 |
| Human_CCR2B | 2501 ATCAACTAAGTGGAGAGAGCCAGGAAGGCTGCATCAGAACCCAGTAAAGC | 2550 |
| Human_CCR2A | 1425 ---------------------------------------------- | 1424 |
| Human_CCR2B | 2551 TTCTTGTCTGGATCTGAGCTGGTTTGTTTTGTGCTTGCTTTTCCCTGCCT | 2600 |
| Human_CCR2A | 1425 ------------------------------AGCCTTTTTCACATAGCT | 1442 |
| Human_CCR2B | 2601 TGCCACTCCCCTCACTCTTCTCTTTTCCCCACAGCCTTTTTCACATAGCT | 2650 |
| Human_CCR2A | 1443 CTTGGCTGTAGGATTGCCCCACTCCAAAAACCAGTGTGTGGAGGTCCAGG | 1492 |
| Human_CCR2B | 2651 CTTGGCTGTAGGATTGCCCCACTCCAAAAACCAGTGTGTGGAGGTCCAGG | 2700 |
| Human_CCR2A | 1493 AGTGAGACCAGGAAAGAATGTGAAAGTGACTACACAAGGACTCCTCGATG | 1542 |
| Human_CCR2B | 2701 AGTGAGACCAGGAAAGAATGTGAAAGTGACTACACAAGGACTCCTCGATG | 2750 |
| Human_CCR2A | 1543 GTCGTGGAAAAGGAAAGTCAATTGGCAGAGCCCTGAAGCCAGTCTTCAG | 1592 |
| Human_CCR2B | 2751 GTCGTGGAAAAGGAAAGTCAATTGGCAGAGCCCTGAAGCCAGTCTTCAG | 2800 |

FIG. 2 (Continued)

```
Human_CCR2A  1593 GACAAAGAAGGAGCCTAGAGACAGAAATGACAGATCTCTGCTTTGGAAAT 1642
                  ||||||||||||||||||||||||||||||||||||||||||||||||||
Human_CCR2B  2801 GACAAAGAAGGAGCCTAGAGACAGAAATGACAGATCTCTGCTTTGGAAAT 2850

Human_CCR2A  1643 CACACGTCTGGCTTCACAGATGTGTGATTCACAGTGTGAATCTTGGTGTC 1692
                  ||||||||||||||||||||||||||||||||||||||||||||||||||
Human_CCR2B  2851 CACACGTCTGGCTTCACAGATGTGTGATTCACAGTGTGAATCTTGGTGTC 2900

Human_CCR2A  1693 TACGTTACCAGGCAGGAAGGCTGAGAGGAGAGAGACTCCAGCTGGGTTGG 1742
                  ||||||||||||||||||||||||||||||||||||||||||||||||||
Human_CCR2B  2901 TACGTTACCAGGCAGGAAGGCTGAGAGGAGAGAGACTCCAGCTGGGTTGG 2950

Human_CCR2A  1743 AAAACAGTATTTTCCAAACTACCTTCCAGTTCCTCATTTTTGAATACAGG 1792
                  ||||||||||||||||||||||||||||||||||||||||||||||||||
Human_CCR2B  2951 AAAACAGTATTTTCCAAACTACCTTCCAGTTCCTCATTTTTGAATACAGG 3000

Human_CCR2A  1793 CATAGAGTTCAGACTTTTTTTAAATAGTAAAAATAAAATTAAAGCTGAAA 1842
                  ||||||||||||||||||||||||||||||||||||||||||||||||||
Human_CCR2B  3001 CATAGAGTTCAGACTTTTTTTAAATAGTAAAAATAAAATTAAAGCTGAAA 3050

Human_CCR2A  1843 ACTGCAACTTGTAAATGTGGTAAAGAGTTAGTTTGAGTTACTATCATGTC 1892
                  ||||||||||||||||||||||||||||||||||||||||||||||||||
Human_CCR2B  3051 ACTGCAACTTGTAAATGTGGTAAAGAGTTAGTTTGAGTTACTATCATGTC 3100

Human_CCR2A  1893 AAACGTGAAAATGCTGTATTAGTCACAGAGATAATTCTAGCTTTGAGCTT 1942
                  ||||||||||||||||||||||||||||||||||||||||||||||||||
Human_CCR2B  3101 AAACGTGAAAATGCTGTATTAGTCACAGAGATAATTCTAGCTTTGAGCTT 3150

Human_CCR2A  1943 AAGAATTTTGAGCAGGTGGTATGTTTGGGAGACTGCTGAGTCAACCCAAT 1992
                  ||||||||||||||||||||||||||||||||||||||||||||||||||
Human_CCR2B  3151 AAGAATTTTGAGCAGGTGGTATGTTTGGGAGACTGCTGAGTCAACCCAAT 3200

Human_CCR2A  1993 AGTTGTTGATTGGCAGGAGTTGGAAGTGTGTGATCTGTGGGCACATTAGC 2042
                  ||||||||||||||||||||||||||||||||||||||||||||||||||
Human_CCR2B  3201 AGTTGTTGATTGGCAGGAGTTGGAAGTGTGTGATCTGTGGGCACATTAGC 3250

Human_CCR2A  2043 CTATGTGCATGCAGCATCTAAGTAATGATGTCGTTTGAATCACAGTATAC 2092
                  ||||||||||||||||||||||||||||||||||||||||||||||||||
Human_CCR2B  3251 CTATGTGCATGCAGCATCTAAGTAATGATGTCGTTTGAATCACAGTATAC 3300

Human_CCR2A  2093 GCTCCATCGCTGTCATCTCAGCTGGATCTCCATTCTCTCAGGCTTGCTGC 2142
                  ||||||||||||||||||||||||||||||||||||||||||||||||||
Human_CCR2B  3301 GCTCCATCGCTGTCATCTCAGCTGGATCTCCATTCTCTCAGGCTTGCTGC 3350
```

FIG. 2 (Continued)

```
Human_CCR2A  2143 CAAAAGCCTTTTGTGTTTTGTTTTGTATCATTATGAAGTCATGCGTTTAA 2192
                  ||||||||||||||||||||||||||||||||||||||||||||||||||
Human_CCR2B  3351 CAAAAGCCTTTTGTGTTTTGTTTTGTATCATTATGAAGTCATGCGTTTAA 3400

Human_CCR2A  2193 TCACATTCGAGTGTTTCAGTGCTTCGCAGATGTCCTTGATGCTCATATTG 2242
                  ||||||||||||||||||||||||||||||||||||||||||||||||||
Human_CCR2B  3401 TCACATTCGAGTGTTTCAGTGCTTCGCAGATGTCCTTGATGCTCATATTG 3450

Human_CCR2A  2243 TTCCCTATTTTGCCAGTGGGAACTCCTAAATCAAGTTGGCTTCTAATCAA 2292
                  ||||||||||||||||||||||||||||||||||||||||||||||||||
Human_CCR2B  3451 TTCCCTATTTTGCCAGTGGGAACTCCTAAATCAAGTTGGCTTCTAATCAA 3500

Human_CCR2A  2293 AGCTTTTAAACCCTATTGGTAAAGAATGGAAGGTGGAGAAGCTCCCTGAA 2342
                  ||||||||||||||||||||||||||||||||||||||||||||||||||
Human_CCR2B  3501 AGCTTTTAAACCCTATTGGTAAAGAATGGAAGGTGGAGAAGCTCCCTGAA 3550

Human_CCR2A  2343 GTAAGCAAAGACTTTCCTCTTAGTCGAGCCAAGTTAAGAATGTTCTTATG 2392
                  ||||||||||||||||||||||||||||||||||||||||||||||||||
Human_CCR2B  3551 GTAAGCAAAGACTTTCCTCTTAGTCGAGCCAAGTTAAGAATGTTCTTATG 3600

Human_CCR2A  2393 TTGCCCAGTGTGTTTCTGATCTGATGCAAGCAAGAAACACTGGGCTTCTA 2442
                  ||||||||||||||||||||||||||||||||||||||||||||||||||
Human_CCR2B  3601 TTGCCCAGTGTGTTTCTGATCTGATGCAAGCAAGAAACACTGGGCTTCTA 3650

Human_CCR2A  2443 GAACCAGGCAACTTGGGAACTAGACTCCCAAGCTGGACTATGGCTCTACT 2492
                  ||||||||||||||||||||||||||||||||||||||||||||||||||
Human_CCR2B  3651 GAACCAGGCAACTTGGGAACTAGACTCCCAAGCTGGACTATGGCTCTACT 3700

Human_CCR2A  2493 TTCAGGCCACATGGCTAAAGAAGGTTTCAGAAAGAAGTGGGACAGAGCA 2542
                  ||||||||||||||||||||||||||||||||||||||||||||||||||
Human_CCR2B  3701 TTCAGGCCACATGGCTAAAGAAGGTTTCAGAAAGAAGTGGGACAGAGCA 3750

Human_CCR2A  2543 GAACTTTCACCTTCATATATTTGTATGATCCTAATGAATGCATAAAATGT 2592
                  ||||||||||||||||||||||||||||||||||||||||||||||||||
Human_CCR2B  3751 GAACTTTCACCTTCATATATTTGTATGATCCTAATGAATGCATAAAATGT 3800

Human_CCR2A  2593 TAAGTTGATGGTGATGAAATGTAAATACTGTTTTTAACAACTATGATTTG 2642
                  ||||||||||||||||||||||||||||||||||||||||||||||||||
Human_CCR2B  3801 TAAGTTGATGGTGATGAAATGTAAATACTGTTTTTAACAACTATGATTTG 3850

Human_CCR2A  2643 GAAAATAAATCAATGCTATAACTATGTTGAAAAAAAAAAAAAAAAA     2689
                  |||||||||||||||||||||||||||||||
Human_CCR2B  3851 GAAAATAAATCAATGCTATAACTATGTTGA-----------------    3880
```

FIG. 2 (Continued)

| rs743660 | rs3918376 | rs41430746 | rs142519963 | rs185882430 |
|---|---|---|---|---|
| rs762788 | rs3918377 | rs41502346 | rs142586851 | rs186259379 |
| rs762789 | rs3918378 | rs41518145 | rs143047415 | rs186727008 |
| rs762790 | rs3918379 | rs55922849 | rs143589710 | rs187021091 |
| rs1042100 | rs3918380 | rs62243000 | rs143987572 | rs188030467 |
| rs1799864 | rs3918381 | rs67450950 | rs145209696 | rs188289723 |
| rs1799865 | rs3918382 | rs71327057 | rs145491896 | rs188527018 |
| rs3092960 | rs3918383 | rs75236779 | rs145700287 | rs188757930 |
| rs3092961 | rs3918384 | rs78257745 | rs145831641 | rs188811375 |
| rs3092962 | rs3918385 | rs80048575 | rs146012105 | rs189083418 |
| rs3092963 | rs3918386 | rs80236415 | rs147945371 | rs190132380 |
| rs3092964 | rs3918387 | rs111312130 | rs148272870 | rs190199583 |
| rs3138042 | rs3918388 | rs112118975 | rs148792928 | rs191292961 |
| rs3749461 | rs4987052 | rs113016448 | rs148861329 | rs191722950 |
| rs3762823 | rs5848794 | rs113112038 | rs149055893 | rs191797612 |
| rs3918354 | rs7640084 | rs113340633 | rs149772269 | rs191926568 |
| rs3918355 | rs10544963 | rs113414873 | rs149826460 | rs192039364 |
| rs3918357 | rs11575061 | rs113539163 | rs150082910 | rs193075921 |
| rs3918358 | rs11575062 | rs113609612 | rs150644817 | rs193254937 |
| rs3918359 | rs11575063 | rs113621946 | rs150767992 | rs199531428 |
| rs3918360 | rs17141046 | rs114700644 | rs150890586 | rs199623670 |
| rs3918361 | rs34041956 | rs138119804 | rs181123418 | rs199666836 |
| rs3918362 | rs34138562 | rs138409969 | rs181429510 | rs199838068 |
| rs3918363 | rs34248467 | rs138568012 | rs181559228 | rs199869211 |
| rs3918364 | rs34693183 | rs138798716 | rs182045635 | rs199884389 |
| rs3918365 | rs34738867 | rs139676582 | rs182278768 | rs200099906 |
| rs3918366 | rs34948438 | rs139853760 | rs182592871 | rs200438087 |
| rs3918367 | rs35402558 | rs140165674 | rs183084727 | rs200491743 |
| rs3918369 | rs35424113 | rs140253702 | rs183410543 | rs200575131 |
| rs3918370 | rs35731127 | rs140800049 | rs184182596 | rs201043108 |
| rs3918371 | rs35836002 | rs140816549 | rs184276075 | rs201140181 |
| rs3918372 | rs36225401 | rs141377703 | rs184336934 | rs201184651 |
| rs3918373 | rs36225727 | rs141700423 | rs184339761 | rs201670838 |
| rs3918374 | rs36225728 | rs141766296 | rs184518086 | rs201767110 |
| rs3918375 | rs41392351 | rs141909499 | rs185364176 | rs201996835 |

FIG. 5

| rs202110859 | rs372883116 | rs527358687 | rs537008568 | rs548185363 |
|---|---|---|---|---|
| rs368137759 | rs373111136 | rs527884713 | rs537173682 | rs548288996 |
| rs368150580 | rs373211972 | rs528266094 | rs537321220 | rs548454578 |
| rs368219093 | rs373266115 | rs528625061 | rs537648329 | rs548516648 |
| rs368302176 | rs373647528 | rs528866403 | rs538240316 | rs548613097 |
| rs368615088 | rs373671614 | rs529452985 | rs538247696 | rs549688502 |
| rs368754451 | rs373811186 | rs529609084 | rs539087679 | rs549709222 |
| rs368842919 | rs373872490 | rs529722242 | rs539379361 | rs549879901 |
| rs369027188 | rs374045702 | rs530047297 | rs539463962 | rs549990114 |
| rs369054907 | rs374222972 | rs530102559 | rs540093336 | rs550274565 |
| rs369188117 | rs374233986 | rs530467796 | rs540741152 | rs550510888 |
| rs369390916 | rs374543178 | rs530798302 | rs541258352 | rs550679672 |
| rs369549053 | rs374603768 | rs530823109 | rs541614093 | rs552269724 |
| rs369723235 | rs374682253 | rs530882456 | rs541727099 | rs552417398 |
| rs370081280 | rs374971443 | rs530885552 | rs542031960 | rs553264714 |
| rs370278890 | rs375466820 | rs531075353 | rs542138875 | rs553718224 |
| rs370462164 | rs375494511 | rs531108767 | rs542253696 | rs553980827 |
| rs370576018 | rs375553715 | rs531468205 | rs543475870 | rs554382556 |
| rs371121141 | rs375566416 | rs531697752 | rs543568405 | rs554581530 |
| rs371138411 | rs375821125 | rs531950442 | rs543643209 | rs554704993 |
| rs371149359 | rs375963547 | rs532015265 | rs544020175 | rs554777802 |
| rs371305652 | rs376017223 | rs532078003 | rs544045612 | rs555409428 |
| rs371486554 | rs376135179 | rs532816630 | rs544742606 | rs556188651 |
| rs371697068 | rs376177514 | rs532880234 | rs545003484 | rs556636324 |
| rs371779665 | rs376593544 | rs532922692 | rs545733068 | rs556697784 |
| rs371790080 | rs376675621 | rs533123132 | rs545782545 | rs556796443 |
| rs371859867 | rs376776685 | rs533538397 | rs545835575 | rs556836673 |
| rs372092396 | rs376867283 | rs534470476 | rs546063212 | rs557061536 |
| rs372095124 | rs376895493 | rs534474700 | rs546559215 | rs557109752 |
| rs372263390 | rs376998166 | rs534745444 | rs547258287 | rs557171085 |
| rs372424162 | rs377141638 | rs535206200 | rs547656527 | rs557767775 |
| rs372553104 | rs377217528 | rs535650424 | rs547752896 | rs558452692 |
| rs372612275 | rs397989433 | rs536377291 | rs547794799 | rs558625213 |
| rs372648667 | rs398062303 | rs536720060 | rs547815439 | rs558691662 |
| rs372758905 | rs527285891 | rs536776017 | rs548077584 | rs559285648 |

FIG. 5 (Continued)

| rs559721780 | rs575514980 | rs749255253 | rs753624537 | rs758441355 |
|---|---|---|---|---|
| rs559793973 | rs575520467 | rs749317568 | rs753655538 | rs758520745 |
| rs561433537 | rs575578713 | rs749369525 | rs753865852 | rs758555738 |
| rs562210983 | rs575970908 | rs749387814 | rs754133368 | rs758632906 |
| rs563372603 | rs576126038 | rs749623975 | rs754321247 | rs758746375 |
| rs565447536 | rs576719179 | rs749834579 | rs754462104 | rs758836764 |
| rs565506818 | rs576746098 | rs750037233 | rs754564513 | rs759124459 |
| rs565638893 | rs576850680 | rs750227804 | rs754702855 | rs759202280 |
| rs565826436 | rs577380670 | rs750425998 | rs754790837 | rs759224501 |
| rs565893556 | rs577442510 | rs750574204 | rs754794357 | rs759501183 |
| rs566027479 | rs577915965 | rs750675458 | rs754874220 | rs759758830 |
| rs566030365 | rs745574295 | rs750765058 | rs755076232 | rs759923582 |
| rs566183903 | rs745672807 | rs750850290 | rs755409798 | rs760146982 |
| rs567078057 | rs745739522 | rs751113907 | rs755716002 | rs760164886 |
| rs567142995 | rs745802485 | rs751150214 | rs755774537 | rs760197238 |
| rs567618909 | rs745833019 | rs751288511 | rs755849824 | rs760208817 |
| rs567805410 | rs745964691 | rs751305081 | rs756006925 | rs760464672 |
| rs567951143 | rs745976186 | rs751438454 | rs756015200 | rs760736040 |
| rs568268057 | rs746334915 | rs751642884 | rs756172205 | rs760787891 |
| rs568691376 | rs746503256 | rs751825867 | rs756220769 | rs760815364 |
| rs569128617 | rs746514238 | rs751927033 | rs756590290 | rs761015332 |
| rs569807797 | rs746791976 | rs751973385 | rs756759016 | rs761033901 |
| rs570856692 | rs747196482 | rs752202072 | rs757086702 | rs761165333 |
| rs571130875 | rs747312276 | rs752368994 | rs757249994 | rs761196602 |
| rs571573968 | rs747406014 | rs752400299 | rs757366142 | rs761283584 |
| rs571965363 | rs747475266 | rs752402950 | rs757413973 | rs761443171 |
| rs572086175 | rs747482058 | rs752458602 | rs757455053 | rs761542862 |
| rs572184287 | rs747673910 | rs752466857 | rs757455917 | rs761571375 |
| rs572418220 | rs747902022 | rs752561542 | rs757459937 | rs761598058 |
| rs573082132 | rs748337154 | rs752746746 | rs757612982 | rs761661605 |
| rs574098686 | rs748444969 | rs752757842 | rs757756160 | rs761771469 |
| rs574162455 | rs748520338 | rs752821656 | rs758002439 | rs761778888 |
| rs574303570 | rs748725992 | rs753151268 | rs758208616 | rs761830240 |
| rs574835423 | rs748913404 | rs753412036 | rs758263706 | rs761861311 |
| rs574992962 | rs749069371 | rs753444273 | rs758316527 | rs762049291 |

FIG. 5 (Continued)

| | | | | |
|---|---|---|---|---|
| rs762239858 | rs766087628 | rs769742268 | rs774215151 | rs778888490 |
| rs762326630 | rs766201549 | rs769801113 | rs774399090 | rs778916097 |
| rs762362055 | rs766403259 | rs769904472 | rs774429903 | rs778974525 |
| rs762411742 | rs766409398 | rs770072742 | rs774603949 | rs778990367 |
| rs762527291 | rs766421784 | rs770140832 | rs774900153 | rs779248623 |
| rs762615152 | rs766571288 | rs770230693 | rs775105678 | rs779255026 |
| rs762616822 | rs766591105 | rs770238230 | rs775193925 | rs779353944 |
| rs762717036 | rs766608058 | rs770681163 | rs775636169 | rs779364631 |
| rs762822542 | rs766867608 | rs770739262 | rs775640963 | rs779381809 |
| rs763317099 | rs766919313 | rs770912248 | rs775682030 | rs779854936 |
| rs763342847 | rs767020440 | rs770943331 | rs775750288 | rs779941455 |
| rs763451379 | rs767147141 | rs771096310 | rs775776254 | rs779943645 |
| rs763472269 | rs767163559 | rs771133369 | rs776011980 | rs780059438 |
| rs763750438 | rs767307595 | rs771219113 | rs776041393 | rs780305808 |
| rs763822597 | rs767422591 | rs771341258 | rs776044125 | rs780393883 |
| rs763904464 | rs767507519 | rs771654222 | rs776234450 | rs780507473 |
| rs763905410 | rs767591344 | rs771670021 | rs776339411 | rs780607505 |
| rs763990194 | rs767602057 | rs771759858 | rs776392870 | rs780628400 |
| rs764006167 | rs767651209 | rs771764372 | rs776605382 | rs780991854 |
| rs764061359 | rs767814989 | rs771947800 | rs776784364 | rs781058166 |
| rs764367612 | rs768098266 | rs772270263 | rs776894646 | rs781080023 |
| rs764685687 | rs768179177 | rs772339032 | rs776999950 | rs781098683 |
| rs764799796 | rs768213330 | rs772392528 | rs777084052 | rs781296283 |
| rs764806372 | rs768542505 | rs772469854 | rs777450040 | rs781349258 |
| rs764868180 | rs768632544 | rs772502682 | rs777623165 | rs781525332 |
| rs764954263 | rs768656901 | rs772590529 | rs777747275 | rs781532254 |
| rs764993818 | rs768825894 | rs772705542 | rs777861286 | rs781615636 |
| rs765062427 | rs768913834 | rs772785853 | rs778126463 | rs781754842 |
| rs765288540 | rs768993464 | rs772789848 | rs778154963 | rs796101293 |
| rs765450675 | rs769023852 | rs772867652 | rs778229598 | rs796453205 |
| rs765628418 | rs769048884 | rs773018725 | rs778431432 | rs865973180 |
| rs765825679 | rs769159836 | rs773284244 | rs778526213 | rs866010913 |
| rs765832227 | rs769171687 | rs773368456 | rs778688821 | rs866260614 |
| rs766030490 | rs769562139 | rs773632891 | rs778700046 | rs866340620 |
| rs766072959 | rs769612183 | rs773943704 | rs778812407 | rs866454124 |

FIG. 5 (Continued)

| rs866870826 | rs891946733 | rs903069356 | rs916225110 | rs928199844 |
|---|---|---|---|---|
| rs866979274 | rs892274638 | rs903506382 | rs916303554 | rs928262971 |
| rs867630389 | rs892345680 | rs903523967 | rs917224190 | rs928701922 |
| rs868594655 | rs892812908 | rs903570595 | rs917368580 | rs928731347 |
| rs868667980 | rs892825682 | rs904001835 | rs918235857 | rs928733166 |
| rs869177412 | rs892926489 | rs904501347 | rs918311505 | rs929504805 |
| rs869196389 | rs893818700 | rs904533778 | rs918401448 | rs929977044 |
| rs879074079 | rs894252021 | rs904647864 | rs919433893 | rs929996139 |
| rs879733984 | rs894316207 | rs905086763 | rs920003975 | rs930044804 |
| rs879887047 | rs894364498 | rs905498558 | rs920217200 | rs930080143 |
| rs886279525 | rs894823975 | rs906537076 | rs920693967 | rs930670334 |
| rs887090155 | rs895046405 | rs907705553 | rs921014396 | rs930979550 |
| rs887129801 | rs895086502 | rs907820425 | rs921410789 | rs931011602 |
| rs887249365 | rs895827596 | rs909327406 | rs921975876 | rs931022413 |
| rs887280664 | rs896080238 | rs909869705 | rs922003762 | rs931073955 |
| rs887330761 | rs896592555 | rs909942185 | rs922186292 | rs931493460 |
| rs887388799 | rs896670559 | rs910295273 | rs922750971 | rs933012780 |
| rs887867491 | rs896797576 | rs910326416 | rs922903374 | rs933023838 |
| rs887889298 | rs896985673 | rs911174121 | rs923013971 | rs933503737 |
| rs887994504 | rs898112838 | rs911379300 | rs923936432 | rs933972856 |
| rs888123102 | rs898118539 | rs911491306 | rs924079447 | rs934050719 |
| rs888190939 | rs898610468 | rs912052418 | rs924192262 | rs934480642 |
| rs888288805 | rs898716571 | rs912192571 | rs924391982 | rs934570573 |
| rs888325656 | rs899112962 | rs912247496 | rs924554270 | rs934979558 |
| rs889288381 | rs899120864 | rs912262629 | rs924597497 | rs935286104 |
| rs889371772 | rs899602136 | rs913351772 | rs925058927 | rs935510475 |
| rs889807466 | rs899968416 | rs913485093 | rs925090228 | rs936074123 |
| rs889839544 | rs900126553 | rs913719014 | rs925202621 | rs936221335 |
| rs890265331 | rs900826664 | rs913789447 | rs925232144 | rs936496823 |
| rs890869952 | rs901027105 | rs914216543 | rs926197709 | rs936946558 |
| rs890921480 | rs901614066 | rs914339831 | rs926247318 | rs938180269 |
| rs891301645 | rs902531149 | rs914498087 | rs926474749 | rs938268924 |
| rs891740602 | rs902562379 | rs915010642 | rs926578593 | rs938729757 |
| rs891803721 | rs902800070 | rs915355564 | rs926602515 | rs938782261 |
| rs891813467 | rs902866315 | rs915897825 | rs927226285 | rs938941328 |

FIG. 5 (Continued)

| rs938956508 | rs950637743 | rs961861316 | rs972112820 | rs984815655 |
|---|---|---|---|---|
| rs939030185 | rs951519498 | rs962056231 | rs972300010 | rs984846240 |
| rs939232657 | rs951647518 | rs962085174 | rs972403675 | rs985326545 |
| rs939256914 | rs951908256 | rs962093482 | rs972556225 | rs985357691 |
| rs940013459 | rs952054519 | rs962570789 | rs972610509 | rs986268815 |
| rs940252379 | rs952230486 | rs962763673 | rs973003582 | rs986989638 |
| rs940778720 | rs952345734 | rs962796119 | rs974474267 | rs987674319 |
| rs940795375 | rs952984524 | rs964050455 | rs975019074 | rs987856949 |
| rs941675500 | rs953650782 | rs964366923 | rs975142662 | rs987956086 |
| rs941706666 | rs953679783 | rs964549680 | rs977286069 | rs987974142 |
| rs942172165 | rs953908733 | rs964570013 | rs977376233 | rs988275731 |
| rs942595054 | rs953943487 | rs964622637 | rs977529526 | rs988832194 |
| rs942684957 | rs953987425 | rs964643335 | rs977532976 | rs988962347 |
| rs942735330 | rs955043705 | rs965061706 | rs978251631 | rs989727710 |
| rs942753961 | rs955388072 | rs965092897 | rs978956880 | rs989966950 |
| rs942784984 | rs955576462 | rs965093789 | rs978989413 | rs989997950 |
| rs943174257 | rs956248695 | rs965599513 | rs979324442 | rs990010044 |
| rs943696925 | rs956413619 | rs966354424 | rs979362408 | rs990492425 |
| rs943707674 | rs956415162 | rs966614047 | rs980109637 | rs990591589 |
| rs943762988 | rs956558557 | rs966641547 | rs980265296 | rs990952226 |
| rs943824772 | rs957078509 | rs967564737 | rs980318913 | rs990983801 |
| rs944187274 | rs957313333 | rs968200507 | rs980333845 | rs991567312 |
| rs944685058 | rs957551454 | rs968607248 | rs980770294 | rs991585973 |
| rs945199806 | rs958274921 | rs968646677 | rs981815564 | rs992051330 |
| rs945205217 | rs958407661 | rs968987199 | rs982279062 | rs992138302 |
| rs945231913 | rs958520464 | rs969057043 | rs982343072 | rs992502489 |
| rs945698509 | rs958550118 | rs969107681 | rs982802239 | rs992593010 |
| rs945730003 | rs959267037 | rs969206738 | rs982850237 | rs992600779 |
| rs946714547 | rs960030529 | rs969237041 | rs982897191 | rs993498773 |
| rs946924089 | rs960196675 | rs969865947 | rs983549686 | rs993589500 |
| rs947900205 | rs960516072 | rs970610680 | rs983731060 | rs993898928 |
| rs948744924 | rs960590644 | rs970702862 | rs983813414 | rs994140893 |
| rs948775939 | rs960679120 | rs971235265 | rs983842894 | rs994753646 |
| rs948995712 | rs961002767 | rs971253495 | rs984285336 | rs995224850 |
| rs949936058 | rs961037063 | rs971414733 | rs984345002 | rs995685448 |

FIG. 5 (Continued)

| rs995763974 | rs1007271829 | rs1018926520 | rs1028332572 | rs1038459145 |
|---|---|---|---|---|
| rs996769493 | rs1007353317 | rs1019025819 | rs1028641470 | rs1038524668 |
| rs997082429 | rs1007945637 | rs1019055651 | rs1029223619 | rs1038923891 |
| rs997142769 | rs1008480849 | rs1019263369 | rs1029230292 | rs1039858709 |
| rs997244239 | rs1008896872 | rs1019401799 | rs1029563748 | rs1039876024 |
| rs998562888 | rs1009027304 | rs1019522925 | rs1029673591 | rs1039963838 |
| rs998721215 | rs1009272994 | rs1019568097 | rs1030148922 | rs1040479974 |
| rs999161581 | rs1009346136 | rs1019832439 | rs1030658938 | rs1040845621 |
| rs1000130725 | rs1009512043 | rs1020376338 | rs1030695518 | rs1040975866 |
| rs1000199976 | rs1009805724 | rs1020491235 | rs1031244393 | rs1041877189 |
| rs1000908711 | rs1009909186 | rs1020940721 | rs1031564546 | rs1042504005 |
| rs1001267279 | rs1010353487 | rs1021495672 | rs1031631905 | rs1042578153 |
| rs1002239525 | rs1010908334 | rs1021661094 | rs1031697885 | rs1042587041 |
| rs1002676850 | rs1011516996 | rs1021931094 | rs1032103024 | rs1042978816 |
| rs1002841311 | rs1011656565 | rs1021959431 | rs1032265105 | rs1043205960 |
| rs1003016095 | rs1011943716 | rs1021994202 | rs1032282883 | rs1043442780 |
| rs1003209435 | rs1011955804 | rs1022386475 | rs1032338138 | rs1043508949 |
| rs1003277914 | rs1012032497 | rs1022947519 | rs1032664318 | rs1043538779 |
| rs1003332112 | rs1012917595 | rs1022954434 | rs1032735926 | rs1043621783 |
| rs1003355536 | rs1013041390 | rs1023013639 | rs1033099663 | rs1044477127 |
| rs1003420442 | rs1013112787 | rs1023344714 | rs1033738684 | rs1044656910 |
| rs1003651330 | rs1013952259 | rs1023448289 | rs1034172057 | rs1044900301 |
| rs1004245965 | rs1014046897 | rs1024017087 | rs1034245577 | rs1045015975 |
| rs1004374514 | rs1014926000 | rs1024031076 | rs1034558812 | rs1045568680 |
| rs1005277051 | rs1015236026 | rs1024376744 | rs1034650133 | rs1045636141 |
| rs1005299124 | rs1015782361 | rs1025320715 | rs1035208851 | rs1046076218 |
| rs1005381254 | rs1016231399 | rs1025362458 | rs1035657487 | rs1047629135 |
| rs1005412540 | rs1016537482 | rs1026223190 | rs1035803279 | rs1047636657 |
| rs1005435668 | rs1016979703 | rs1026481655 | rs1035908022 | rs1048010290 |
| rs1006452249 | rs1017047008 | rs1027219083 | rs1036467232 | rs1048083285 |
| rs1006484657 | rs1017546867 | rs1027661276 | rs1036730719 | rs1048117503 |
| rs1006760624 | rs1018252946 | rs1027844724 | rs1036800454 | rs1048173967 |
| rs1006864588 | rs1018480172 | rs1027989068 | rs1036939456 | rs1048627793 |
| rs1006896946 | rs1018544727 | rs1028074174 | rs1037906840 | rs1048659789 |
| rs1007094596 | rs1018554346 | rs1028253341 | rs1038398032 | rs1049177514 |

FIG. 5 (Continued)

| |
|---|
| rs1049213422 |
| rs1049518517 |
| rs1049552646 |
| rs1049616956 |
| rs1051068981 |
| rs1051121806 |
| rs1051692426 |
| rs1051793414 |
| rs1052091503 |
| rs1052195779 |
| rs1052313643 |
| rs1053170053 |
| rs1053301608 |
| rs1053593576 |
| rs1053726972 |
| rs1054083531 |
| rs1054147142 |
| rs1054657500 |
| rs1055084032 |
| rs1055295682 |
| rs1055653324 |
| rs1055685011 |
| rs1056210957 |
| rs1056337617 |
| rs1056769737 |
| rs1057359447 |
| rs1057460916 |

FIG. 5 (Continued)

SEQUENCE LISTING

<160> NUMBER OF SEQ ID NOS: 28

<210> SEQ ID NO 1
<211> LENGTH: 2689
<212> TYPE: DNA
<213> ORGANISM: Artificial Sequence
<220> FEATURE:
<223> OTHER INFORMATION: Homo sapiens, CCR2 isoform A cDNA

<400> SEQUENCE: 1

| | | | | | |
|---|---|---|---|---|---|
| tttattctct | ggaacatgaa | acattctgtt | gtgctcatat | catgcaaatt | atcactagta | 60 |
| ggagagcaga | gagtggaaat | gttccaggta | taaagaccca | caagataaag | aagctcagag | 120 |
| tcgttagaaa | caggagcaga | tgtacagggt | ttgcctgact | cacactcaag | gttgcataag | 180 |
| caagatttca | aaattaatcc | tattctggag | acctcaaccc | aatgtacaat | gttcctgact | 240 |
| ggaaagaag | aactatattt | ttctgatttt | tttttcaaa | tctttaccat | tagttgccct | 300 |
| gtatctccgc | cttcactttc | tgcaggaaac | tttattcct | acttctgcat | gccaagtttc | 360 |
| tacctctaga | tctgtttggt | tcagttgctg | agaagcctga | cataccagga | ctgcctgaga | 420 |
| caagccacaa | gctgaacaga | gaaagtggat | tgaacaagga | cgcatttccc | cagtacatcc | 480 |
| acaacatgct | gtccacatct | cgttctcggt | ttatcagaaa | taccaacgag | agcggtgaag | 540 |
| aagtcaccac | ctttttgat | tatgattacg | gtgctccctg | tcataaattt | gacgtgaagc | 600 |
| aaattggggc | ccaactcctg | cctccgctct | actcgctggt | gttcatcttt | ggttttgtgg | 660 |
| gcaacatgct | ggtcgtcctc | atcttaataa | actgcaaaaa | gctgaagtgc | ttgactgaca | 720 |
| tttacctgct | caacctggcc | atctctgatc | tgcttttct | tattactctc | ccattgtggg | 780 |
| ctcactctgc | tgcaaatgag | tgggtctttg | gaatgcaat | gtgcaaatta | ttcacagggc | 840 |
| tgtatcacat | cggttatttt | ggcggaatct | tcttcatcat | cctcctgaca | atcgatagat | 900 |
| acctggctat | tgtccatgct | gtgtttgctt | taaaagccag | gacggtcacc | tttggggtgg | 960 |
| tgacaagtgt | gatcacctgg | ttggtggctg | tgtttgcttc | tgtcccagga | atcatcttta | 1020 |
| ctaaatgcca | gaaagaagat | tctgtttatg | tctgtggccc | ttattttcca | cgaggatgga | 1080 |
| ataatttcca | cacaataatg | aggaacattt | tggggctggt | cctgccgctg | ctcatcatgg | 1140 |
| tcatctgcta | ctcgggaatc | ctgaaaaccc | tgcttcggtg | tcgaaacgag | aagaagaggc | 1200 |
| atagggcagt | gagagtcatc | ttcaccatca | tgattgttta | ctttctcttc | tggactccct | 1260 |
| ataatattgt | cattctcctg | aacaccttcc | aggaattctt | cggcctgagt | aactgtgaaa | 1320 |
| gcaccagtca | actggaccaa | gccacgcagg | tgacagagac | tcttgggatg | actcactgct | 1380 |
| gcatcaatcc | catcatctat | gccttcgttg | gggagaagtt | cagaagcctt | tttcacatag | 1440 |
| ctcttggctg | taggattgcc | ccactccaaa | aaccagtgtg | tggaggtcca | ggagtgagac | 1500 |
| caggaaagaa | tgtgaaagtg | actacacaag | gactcctcga | tggtcgtgga | aaaggaaagt | 1560 |
| caattggcag | agcccctgaa | gccagtcttc | aggacaaaga | aggagcctag | agacagaaat | 1620 |
| gacagatctc | tgctttggaa | atcacacgtc | tggcttcaca | gatgtgtgat | tcacagtgtg | 1680 |
| aatcttggtg | tctacgttac | caggcaggaa | ggctgagagg | agagagactc | cagctgggtt | 1740 |
| ggaaaacagt | attttccaaa | ctaccttcca | gttcctcatt | tttgaataca | ggcatagagt | 1800 |
| tcagactttt | tttaaatagt | aaaaataaaa | ttaaagctga | aaactgcaac | ttgtaaatgt | 1860 |
| ggtaaagagt | tagtttgagt | tactatcatg | tcaaacgtga | aaatgctgta | ttagtcacag | 1920 |
| agataattct | agctttgagc | ttaagaaattt | tgagcaggtg | gtatgtttgg | gagactgctg | 1980 |
| agtcaaccca | atagttgttg | attggcagga | gttggaagtg | tgtgatctgt | gggcacatta | 2040 |

```
gcctatgtgc atgcagcatc taagtaatga tgtcgtttga atcacagtat acgctccatc    2100
gctgtcatct cagctggatc tccattctct caggcttgct gccaaaagcc ttttgtgttt    2160
tgttttgtat cattatgaag tcatgcgttt aatcacattc gagtgtttca gtgcttcgca    2220
gatgtccttg atgctcatat tgttccctat tttgccagtg ggaactccta aatcaagttg    2280
gcttctaatc aaagctttta aaccctattg gtaaagaatg gaaggtggag aagctccctg    2340
aagtaagcaa agacttttcct cttagtcgag ccaagttaag aatgttctta tgttgcccag    2400
tgtgtttctg atctgatgca agcaagaaac actgggcttc tagaaccagg caacttggga    2460
actagactcc caagctggac tatggctcta ctttcaggcc acatggctaa agaaggtttc    2520
agaaagaagt ggggacagag cagaactttc accttcatat atttgtatga tcctaatgaa    2580
tgcataaaat gttaagttga tggtgatgaa atgtaaatac tgttttttaac aactatgatt    2640 tggaaaataa atcaatgcta taactatgtt gaaaaaaaaa aaaaaaaa                  2689
```

```
<210> SEQ ID NO 2
<211> LENGTH: 2689
<212> TYPE: RNA
<213> ORGANISM: Homo sapiens

<400> SEQUENCE: 2
```

```
uuuauucucu ggaacaugaa acauucuguu gugcucauau caugcaaauu aucacuagua      60
ggagagcaga gaguggaaau guuccaggua uaaagaccca caagauaaag aagcucagag     120
ucguuagaaa caggagcaga guacaggguu ugccugacu cacacucaag guugcauaag     180
caagauuuca aaauuaaucc uauucuggag acccuaaccc aauguacaau guuccugacu     240
ggaaaagaag aacuauauuu uucugauuuu uuuuucaaa ucuuuaccau uaguugcccu      300
guaucuccgc cuucacuuuc ugcaggaaac uuuauuccu acuucugcau gccaaguuuc      360
uaccucuaga ucuguuuggu ucaguugcug agaagcccuga cauaccagga cugccugaga     420
caagccacaa gcugaacaga gaaaguggau ugaacaagga cgcauuuccc caguacaucc     480
acaacaugcu guccacaucu cguucucggu uuaucagaaa uaccaacgag agcggugaag     540
aagucaccac cuuuuuugau uaugauuacg gugcucccug ucauaaauuu gacgugaagc     600
aaauuggggc ccaacuccug ccuccgcucu acucgcuggu uucaucuuu gguuuugugg     660 gcaacaugcu ggucguccuc aucuuaauaa acugcaaaaa gcugaagugc uugacugaca     720
uuuaccugcu caaccuggcc aucucugauc ugcuuuuucu uauuacucuc ccauugugug     780
cucacucugc ugcaaaugag ugggucuuug ggaaugcaau gugcaaauua ucacagggc      840 uguaucacau cgguuauuuu ggcggaaucu cuucaucau ccuccugaca aucgauagau      900
accuggcuau uguccaugcu guguuugcuu uaaaagccag gacggucacc uuggggugg      960 ugacaagugu gaucaccugg uuggugcug uguugcuuc ugucccagga aucaucuuua    1020
cuaaaugcca gaaagaagau ucuguuuaug ucuggccc uuauuuucca cgaggaugga    1080
auaauuucca cacaauaaug aggaacauuu uggggcuggu ccugccgcug cucaucaugg    1140
ucaucugcua ucgggaauc cugaaaaccc ugcuucggug ucgaaacgag aagaagaggc    1200
auagggcagu gagagucauc uucaccauca ugauuguuua cuucucuuc uggacucccu    1260 auaauauugu cauucuccug aacaccuucc aggaauucuu cggccugagu aacugugaaa    1320
gcaccaguca acuggaccaa gccacgcagg ugacagagac ucuugggaug acucacgcu    1380 gcaucaaucc caucaucuau gccuucguug gggagaaguu cagaagccuu uuucacauag    1440
```

```
cucuuggcug uaggauugcc ccacuccaaa aaccagugug uggaggucca ggagugagac    1500
caggaaagaa ugugaaagug acuacacaag gacuccucga uggucgugga aaaggaaagu    1560
caauuggcag agccccugaa gccagucuuc aggacaaaga aggagccuag agacagaaau    1620
gacagaucuc ugcuuuggaa aucacacguc uggcuucaca gaugugugau cacagugug     1680 aaucuuggug ucuacguuac caggcaggaa ggcugagagg agagagacuc cagcuggguu    1740
ggaaaacagu auuuuccaaa cuaccuucca guuccucauu uuugaauaca ggcauagagu    1800
ucagacuuuu uuuaaauagu aaaaauaaaa uuaaagcuga aaacugcaac uuguaaaugu    1860
gguaaagagu uaguuugagu acuaucaug ucaaacguga aaaugcugua uuagucacag     1920
agauaauucu agcuuugagc uuaagaauuu ugagcaggug uauguuugg gagacugcug     1980 agucaaccca auaguuguug auuggcagga guuggaagug ugugaucugu gggcacauua    2040
gccuaugugc augcagcauc uaaguaauga ugucguuuga aucacaguau acgcuccauc    2100
gcugucaucu cagcuggauc uccauucucu caggcuugcu gccaaaagcc uuuuguguuu    2160
uguuuuguau cauuaugaag ucaugcguuu aaucacauuc gaguguuuca gugcuucgca    2220
gauguccuug augcucauau uguucccuau uuugccagug ggaacuccua aaucaaguug    2280
gcuucuaauc aaagcuuuua aacccuauug guaaagaaug aagguggag aagcucccug     2340 aaguaagcaa agacuuuccu cuuagucgag ccaaguuaag aauguucuua uguugcccag    2400
uguguuucug aucugaugca agcaagaaac acugggcuuc uagaaccagg caacuuggga    2460
acuagacucc caagcuggac uauggcucua cuuucaggcc acauggcuaa agaagguuuc    2520
agaaagaagu ggggacagag cagaacuuuc accuucauau auuuguauga uccuaaugaa    2580
ugcauaaaau guuaaguuga uggugaugaa auguaaauac uguuuuuaac aacuaugauu    2640
uggaaaauaa aucaaugcua uaacuauguu gaaaaaaaaa aaaaaaaa                2689
```

<210> SEQ ID NO 3
<211> LENGTH: 374
<212> TYPE: PRT
<213> ORGANISM: Homo sapiens

<400> SEQUENCE: 3

```
Met Leu Ser Thr Ser Arg Ser Arg Phe Ile Arg Asn Thr Asn Glu Ser
1               5                   10                  15

Gly Glu Glu Val Thr Thr Phe Phe Asp Tyr Asp Tyr Gly Ala Pro Cys
                20                  25                  30

His Lys Phe Asp Val Lys Gln Ile Gly Ala Gln Leu Leu Pro Pro Leu
            35                  40                  45

Tyr Ser Leu Val Phe Ile Phe Gly Phe Val Gly Asn Met Leu Val Val
        50                  55                  60

Leu Ile Leu Ile Asn Cys Lys Lys Leu Lys Cys Leu Thr Asp Ile Tyr
65                  70                  75                  80

Leu Leu Asn Leu Ala Ile Ser Asp Leu Leu Phe Leu Ile Thr Leu Pro
                85                  90                  95

Leu Trp Ala His Ser Ala Ala Asn Glu Trp Val Phe Gly Asn Ala Met
            100                 105                 110

Cys Lys Leu Phe Thr Gly Leu Tyr His Ile Gly Tyr Phe Gly Gly Ile
        115                 120                 125

Phe Phe Ile Ile Leu Leu Thr Ile Asp Arg Tyr Leu Ala Ile Val His
    130                 135                 140

Ala Val Phe Ala Leu Lys Ala Arg Thr Val Thr Phe Gly Val Val Thr
145                 150                 155                 160
```

Ser Val Ile Thr Trp Leu Val Ala Val Phe Ala Ser Val Pro Gly Ile
            165                 170                 175

Ile Phe Thr Lys Cys Gln Lys Glu Asp Ser Val Tyr Val Cys Gly Pro
        180                 185                 190

Tyr Phe Pro Arg Gly Trp Asn Asn Phe His Thr Ile Met Arg Asn Ile
    195                 200                 205

Leu Gly Leu Val Leu Pro Leu Leu Ile Met Val Ile Cys Tyr Ser Gly
210                 215                 220

Ile Leu Lys Thr Leu Leu Arg Cys Arg Asn Glu Lys Lys Arg His Arg
225                 230                 235                 240

Ala Val Arg Val Ile Phe Thr Ile Met Ile Val Tyr Phe Leu Phe Trp
                245                 250                 255

Thr Pro Tyr Asn Ile Val Ile Leu Leu Asn Thr Phe Gln Glu Phe Phe
            260                 265                 270

Gly Leu Ser Asn Cys Glu Ser Thr Ser Gln Leu Asp Gln Ala Thr Gln
        275                 280                 285

Val Thr Glu Thr Leu Gly Met Thr His Cys Cys Ile Asn Pro Ile Ile
    290                 295                 300

Tyr Ala Phe Val Gly Glu Lys Phe Arg Ser Leu Phe His Ile Ala Leu
305                 310                 315                 320

Gly Cys Arg Ile Ala Pro Leu Gln Lys Pro Val Cys Gly Gly Pro Gly
                325                 330                 335

Val Arg Pro Gly Lys Asn Val Lys Val Thr Thr Gln Gly Leu Leu Asp
            340                 345                 350

Gly Arg Gly Lys Gly Lys Ser Ile Gly Arg Ala Pro Glu Ala Ser Leu
        355                 360                 365

Gln Asp Lys Glu Gly Ala
    370

<210> SEQ ID NO 4
<211> LENGTH: 3880
<212> TYPE: DNA
<213> ORGANISM: Artificial Sequence
<220> FEATURE:
<223> OTHER INFORMATION: Homo Sapiens, CCR2 isoform B cDNA

<400> SEQUENCE: 4
tttattctct ggaacatgaa acattctgtt gtgctcatat catgcaaatt atcactagta        60
ggagagcaga gagtggaaat gttccaggta taaagaccca caagataaag aagctcagag       120
tcgttagaaa caggagcaga tgtacagggt ttgcctgact cacactcaag gttgcataag       180
caagatttca aaattaatcc tattctggag acctcaaccc aatgtacaat gttcctgact       240
ggaaaagaag aactatattt ttctgatttt ttttttcaaa tctttaccat tagttgccct       300
gtatctccgc cttcactttc tgcaggaaac tttatttcct acttctgcat gccaagtttc       360
tacctctaga tctgtttggt tcagttgctg agaagcctga cataccagga ctgcctgaga       420
caagccacaa gctgaacaga gaaagtggat tgaacaagga cgcatttccc cagtacatcc       480
acaacatgct gtccacatct cgttctcggt ttatcagaaa taccaacgag agcggtgaag       540
aagtcaccac cttttttgat tatgattacg gtgctccctg tcataaattt gacgtgaagc       600
aaattggggc ccaactcctg cctccgctct actcgctggt gttcatcttt ggttttgtgg       660
gcaacatgct ggtcgtcctc atcttaataa actgcaaaaa gctgaagtgc ttgactgaca       720
tttacctgct caacctggcc atctctgatc tgcttttttct tattactctc ccattgtggg       780

```
ctcactctgc tgcaaatgag tgggtctttg ggaatgcaat gtgcaaatta ttcacagggc      840
tgtatcacat cggttatttt ggcggaatct tcttcatcat cctcctgaca atcgatagat      900
acctggctat tgtccatgct gtgtttgctt aaaaagccag gacggtcacc tttggggtgg      960
tgacaagtgt gatcacctgg ttggtggctg tgtttgcttc tgtcccagga atcatcttta     1020
ctaaatgcca gaaagaagat tctgtttatg tctgtggccc ttattttcca cgaggatgga     1080
ataatttcca cacaataatg aggaacattt tggggctggt cctgccgctg ctcatcatgg     1140
tcatctgcta ctcgggaatc ctgaaaaccc tgcttcggtg tcgaaacgag aagaagaggc     1200
atagggcagt gagagtcatc ttcaccatca tgattgttta ctttctcttc tggactccct     1260
ataatattgt cattctcctg aacaccttcc aggaattctt cggcctgagt aactgtgaaa     1320
gcaccagtca actggaccaa gccacgcagg tgacagagac tcttgggatg actcactgct     1380
gcatcaatcc catcatctat gccttcgttg gggagaagtt cagaaggtat ctctcggtgt     1440
tcttccgaaa gcacatcacc aagcgcttct gcaaacaatg tccagttttc tacagggaga     1500
cagtggatgg agtgacttca acaaacacgc cttccactgg ggagcaggaa gtctcggctg     1560
gtttataaaa cgaggagcag tttgattgtt gtttataaag ggagataaca atctgtatat     1620
aacaacaaac ttcaagggtt tgttaacaa tagaaacctg taaagcaggt gcccaggaac     1680
ctcagggctg tgtgtactaa tacagactat gtcacccaat gcatatccaa catgtgctca     1740
gggaataatc cagaaaaact gtgggtagag actttgactc tccagaaagc tcatctcagc     1800
tcctgaaaaa tgcctcatta ccttgtgcta atcctctttt tctagtcttc ataatttctt     1860
cactcaatct ctgattctgt caatgtcttg aaatcaaggg ccagctggag gtgaagaaga     1920
gaatgtgaca ggcacagatg aatgggagtg agggatagtg gggtcagggc tgagaggaga     1980
aggagggaga catgagcatg gctgagcctg acaaagaca aaggtgagca aagggctcac     2040
gcattcagcc aggagatgat actggtcctt agccccatct gccacgtgta tttaaccttg     2100
aagggttcac caggtcaggg agagtttggg aactgcaata acctgggagt tttggtggag     2160
tccgatgatt ctcttttgca taagtgcatg acatattttt gctttattac agtttatcta     2220
tggcacccat gcaccttaca tttgaaatct atgaaatatc atgctccatt gttcagatgc     2280
ttcttaggcc acatcccct gtctaaaaat tcagaaaatt tttgtttata aagatgcat      2340
tatctatgat atgctaatat atgtatatgc aatatatata ggctcttgct tgatctctcc     2400
aggaggtagt gattatgaga aggggtgga gaatgatgag ttccttcacc aggagcaaag     2460
gacgggatc gtgtggaacc actgcagaac tatttccgaa atcaactaag tggagagagc     2520
caggaaggct gcatcagaac ccagtaaagc ttcttgtctg gatctgagct ggtttgtttt     2580
gtgcttgctt ttccctgcct tgccactccc ctcactcttc tcttttcccc acagccttt      2640
tcacatagct cttggctgta ggattgcccc actccaaaaa ccagtgtgtg gaggtccagg     2700
agtgagacca ggaaagaatg tgaaagtgac tacacaagga ctcctcgatg gtcgtggaaa     2760
aggaaagtca attggcagag cccctgaagc cagtcttcag gacaaagaag gagcctagag    2820
acagaaatga cagatctctg ctttggaaat cacacgtctg gcttcacaga tgtgtgattc     2880
acagtgtgaa tcttggtgtc tacgttacca ggcaggaagg ctgagaggag agagactcca     2940
gctgggttgg aaaacagtat tttccaaact accttccagt tcctcatttt tgaatacagg     3000
catagagttc agactttttt taaatagtaa aaataaaatt aaagctgaaa actgcaactt     3060
gtaaatgtgt taaagagtta gtttgagtta ctatcatgtc aaacgtgaaa atgctgtatt     3120
agtcacagag ataattctag ctttgagctt aagaattttg agcaggtggt atgtttggga     3180
```

| | |
|---|---|
| gactgctgag tcaacccaat agttgttgat tggcaggagt tggaagtgtg tgatctgtgg | 3240 |
| gcacattagc ctatgtgcat gcagcatcta agtaatgatg tcgtttgaat cacagtatac | 3300 |
| gctccatcgc tgtcatctca gctggatctc cattctctca ggcttgctgc caaaagcctt | 3360 |
| ttgtgttttg ttttgtatca ttatgaagtc atgcgtttaa tcacattcga gtgtttcagt | 3420 |
| gcttcgcaga tgtccttgat gctcatattg ttccctattt tgccagtggg aactcctaaa | 3480 |
| tcaagttggc ttctaatcaa agcttttaaa cccctattggt aaagaatgga aggtggagaa | 3540 |
| gctccctgaa gtaagcaaag actttcctct tagtcgagcc aagttaagaa tgttcttatg | 3600 |
| ttgcccagtg tgtttctgat ctgatgcaag caagaaacac tgggcttcta gaaccaggca | 3660 |
| acttgggaac tagactccca agctggacta tggctctact ttcaggccac atggctaaag | 3720 |
| aaggtttcag aaagaagtgg ggacagagca gaactttcac cttcatatat ttgtatgatc | 3780 |
| ctaatgaatg cataaaatgt taagttgatg gtgatgaaat gtaaatactg tttttaacaa | 3840 |
| ctatgatttg gaaaataaat caatgctata actatgttga | 3880 |

<210> SEQ ID NO 5
<211> LENGTH: 3880
<212> TYPE: RNA
<213> ORGANISM: Homo sapiens

<400> SEQUENCE: 5

| | |
|---|---|
| uuuauucucu ggaacaugaa acauucuguu gugcucauau caugcaaauu aucacuagua | 60 |
| ggagagcaga gaguggaaau guuccaggua uaaagaccca caagauaaag aagcucagag | 120 |
| ucguuagaaa caggagcaga guacagggu uugccugacu cacacucaag guugcauaag | 180 |
| caagauuuca aaauuaaucc uauucuggag accuaacccc aaguguacaau guuccugacu | 240 |
| ggaaaagaag aacuauauuu uucugauuuu uuuuucaaa ucuuuaccau uaguugcccu | 300 |
| guaucuccgc cuucacuuuc ugcaggaaac uuuauuccu acuucugcau gccaaguuuc | 360 |
| uaccucuaga ucuguuuggu ucaguugcug agaagccuga cauaccagga cugccugaga | 420 |
| caagccacaa gcugaacaga gaaaguggau ugaacaagga cgcauuuccc caguacaucc | 480 |
| acaacaugcu guccaucucu cguucucggu uuaucagaaa uaccaacgag agcggugaag | 540 |
| aagucaccac cuuuuuugau uaugauuacg gugcucccug ucauaaauuu gacgugaagc | 600 |
| aaauuggggc ccaacuccug ccuccgcucu acucgcuggu uucaucuuu gguuugugg | 660 |
| gcaacaugcu ggucguccuc aucuuaauaa acugcaaaaa gcugaagugc uugacugaca | 720 |
| uuuaccugcu caaccuggcc aucucugauc ugcuuuuucu uauuacucuc ccauuguggg | 780 |
| cucacucugc ugcaaaugag uggguucuug ggaaugcaau gugcaaauua ucacagggc | 840 |
| uguaucacau cgguuauuuu gcggaaucu cuucaucau ccuccugaca aucgauagau | 900 |
| accuggcuau uguccaugcu guguuugcuu aaaagccag gacggucacc uuuggggugg | 960 |
| ugacaagugu gauccaccugg uugguggcug uguugcuuc ugucccagga aucaucuuua | 1020 |
| cuaaaugcca gaaagaagau ucuguuuaug ucuguggccc uuauuuucca cgaggaugga | 1080 |
| auaauuucca cacaauaaug aggaacauuu uggggcuggu ccugccgcug cucaucaugg | 1140 |
| ucaucugcua cucgggaauc cugaaaaccc ugcuucggu cgaaacgag aagaagaggc | 1200 |
| auagggcagu gagagucauc uucaccauca ugauuguuua cuuucucuuc uggacucccu | 1260 |
| auaauauugu cauucuccug aacaccuucc aggaauucuu cggccugagu aacuguaaa | 1320 |
| gcaccaguca acuggaccaa gccacgcagg ugacagagac ucuugggaug acucacugcu | 1380 |

```
gcaucaauccc caucaucuau gccuucguug ggagaaguu cagaagguau cucucggugu    1440
ucuuccgaaa gcacaucacc aagcgcuucu gcaaacaaug uccaguuuuc uacagggaga    1500
caguggaugg agugacuuca acaaacacgc cuuccacugg ggagcaggaa gucucggcug    1560
guuuauaaaa cgaggagcag uuugauuguu guuuauaaag ggagauaaca aucuguauau    1620
aacaacaaac uucaaggguu uguugaacaa uagaaaccug uaaagcaggu gcccaggaac    1680
cucagggcug uguguacuaa uacagacuau gucacccaau gcauauccaa caugugcuca    1740
gggaauaauc cagaaaaacu gugggguagag acuuugacuc uccagaaagc ucaucucagc    1800
uccugaaaaa ugccucauua ccuugugcua auccucuuuu ucuagucuuc auaauuucuu    1860
cacucaaucu cugauucugu caaugucuug aaaucaaggg ccagcuggag gugaagaaga    1920
gaaugugaca ggcacagaug aaugggagug agggauagug gggucagggc ugagaggaga    1980
aggagggaga caugagcaug gcugagccug gacaaagaca aaggugagca aagggcucac    2040
gcauucagcc aggagaugau acuggucccuu agccccaucu gccacgcugua uuuaaccuug    2100 aagggguucac caggucaggg agaguuuggg aacugcaaua accgggagu uugguggag    2160 uccgaugauu cucuuuugca uaagugcaug acauauuuuu gcuuuauuac aguuuaucua    2220
uggcacccau gcaccuuaca uuugaaaucu augaaauauc augcuccauu guucagaugc    2280
uucuuaggcc acauccccu gucuaaaaau ucagaaaauu uuuguuuaua aaagaugcau    2340
uaucuaugau augcuaauau auguauaugc aauauauaua ggcucuugcu ugaucucucc    2400
aggagguagu gauuaugaga agggggugga gaaugaugag uuccuucacc aggagcaaag    2460
gacggggauc guguggaacc acugcagaac uauuuccgaa aucaacuaag uggagagagc    2520
caggaaggcu gcaucagaac ccaguaaagc uucuugucug gaucugagcu gguuuguuuu    2580
gugcuugcuu uucccugccu ugccacuccc cucacucuuc ucuuuccccc acagccuuuu    2640
ucacauagcu cuuggcugua ggauugcccc acuccaaaaa ccagugugug gagguccagg    2700
agugagacca ggaaagaaug ugaaagugac uacacaagga cuccgcgaug gucguggaaa    2760
aggaaagucu auuggcagag cccuugaagc cagucuucag gacaaagaag gagccuagag    2820
acagaaauga cagaucucug cuuuggaaau cacacgucug gcuucacaga ugugugauuc    2880
acagugugaa ucuggugucu uacguuacca ggcaggaagg cugagaggag agagacucca    2940
gcugggguug aaaacaguau uuccaaacu accuuccagu uccucauuuu ugaauacagg    3000
cauagaguuc agacuuuuuu uaaauaguaa aaauaaaauu aaagcugaaa acugcaacuu    3060
guaaaugugg uaaagaguua guugaguua cuaucaugu aaacgugaaa augcuguauu    3120
agucacagag auaauucuag cuuugagcuu aagaauuuug agcagguggu auguuuggga    3180
gacugcugag ucaacccaau aguuguugau uggcaggagu uggaagugug ugaucugugg    3240
gcacauuagc cuaugugcau gcagcaucua aguaaugaug ucguugaau cacaguauac    3300 gcuccaucgc ugucaucuca gcuggaucuc cauucucuca ggcuugcugc caaaagccuu    3360
uuguguuuug uuuuguauca uuaugaaguc augcguuuaa ucacauucga guguuucagu    3420
gcuucgcaga uguccuugau gcucauauug uucccuauuu ugccagugg aacuccuaaa    3480 ucaaguggcu uucuaaucaa agcuuuuaaa cccauugguu aaagaauggaa aggugggaga    3540 gcucccugaa guaagcaaag acuuuccucu uagucgagcc aaguuaagaa uguucuuaug    3600
uugcccagug uguuucugau cugaugcaag caagaaacac ugggcuucua gaaccaggca    3660
acuugggaac uagacucccca agcuggacua uggcucuacu uucaggccac auggcuaaag    3720
aagguuucag aaagaagugg ggacagagca gaacuuucac cuucauauau uuguaugauc    3780
```

```
cuaaugaaug cauaaaaugu uaaguugaug gugaugaaau guaaauacug uuuuuaacaa    3840
cuaugauuug gaaaauaaau caaugcuaua acuauguuga                          3880
```

<210> SEQ ID NO 6
<211> LENGTH: 360
<212> TYPE: PRT
<213> ORGANISM: Homo sapiens

<400> SEQUENCE: 6

```
Met Leu Ser Thr Ser Arg Ser Arg Phe Ile Arg Asn Thr Asn Glu Ser
1               5                   10                  15

Gly Glu Glu Val Thr Thr Phe Phe Asp Tyr Asp Tyr Gly Ala Pro Cys
            20                  25                  30

His Lys Phe Asp Val Lys Gln Ile Gly Ala Gln Leu Leu Pro Pro Leu
        35                  40                  45

Tyr Ser Leu Val Phe Ile Phe Gly Phe Val Gly Asn Met Leu Val Val
    50                  55                  60

Leu Ile Leu Ile Asn Cys Lys Lys Leu Lys Cys Leu Thr Asp Ile Tyr
65                  70                  75                  80

Leu Leu Asn Leu Ala Ile Ser Asp Leu Leu Phe Leu Ile Thr Leu Pro
                85                  90                  95

Leu Trp Ala His Ser Ala Ala Asn Glu Trp Val Phe Gly Asn Ala Met
            100                 105                 110

Cys Lys Leu Phe Thr Gly Leu Tyr His Ile Gly Tyr Phe Gly Gly Ile
        115                 120                 125

Phe Phe Ile Ile Leu Leu Thr Ile Asp Arg Tyr Leu Ala Ile Val His
    130                 135                 140

Ala Val Phe Ala Leu Lys Ala Arg Thr Val Thr Phe Gly Val Val Thr
145                 150                 155                 160

Ser Val Ile Thr Trp Leu Val Ala Val Phe Ala Ser Val Pro Gly Ile
                165                 170                 175

Ile Phe Thr Lys Cys Gln Lys Glu Asp Ser Val Tyr Val Cys Gly Pro
            180                 185                 190

Tyr Phe Pro Arg Gly Trp Asn Asn Phe His Thr Ile Met Arg Asn Ile
        195                 200                 205

Leu Gly Leu Val Leu Pro Leu Leu Ile Met Val Ile Cys Tyr Ser Gly
    210                 215                 220

Ile Leu Lys Thr Leu Leu Arg Cys Arg Asn Glu Lys Lys Arg His Arg
225                 230                 235                 240

Ala Val Arg Val Ile Phe Thr Ile Met Ile Val Tyr Phe Leu Phe Trp
                245                 250                 255

Thr Pro Tyr Asn Ile Val Ile Leu Leu Asn Thr Phe Gln Glu Phe Phe
            260                 265                 270

Gly Leu Ser Asn Cys Glu Ser Thr Ser Gln Leu Asp Gln Ala Thr Gln
        275                 280                 285

Val Thr Glu Thr Leu Gly Met Thr His Cys Cys Ile Asn Pro Ile Ile
    290                 295                 300

Tyr Ala Phe Val Gly Glu Lys Phe Arg Arg Tyr Leu Ser Val Phe Phe
305                 310                 315                 320

Arg Lys His Ile Thr Lys Arg Phe Cys Lys Gln Cys Pro Val Phe Tyr
                325                 330                 335

Arg Glu Thr Val Asp Gly Val Ser Thr Asn Thr Pro Ser Thr Gly
            340                 345                 350
```

-continued

Glu Gln Glu Val Ser Ala Gly Leu
            355                 360

<210> SEQ ID NO 7
<211> LENGTH: 21
<212> TYPE: DNA
<213> ORGANISM: Artificial Sequence
<220> FEATURE:
<223> OTHER INFORMATION: Forward primer; Primer code: C

<400> SEQUENCE: 7
tagggcagtg agagtcatct t                                        21

<210> SEQ ID NO 8
<211> LENGTH: 21
<212> TYPE: DNA
<213> ORGANISM: Artificial Sequence
<220> FEATURE:
<223> OTHER INFORMATION: Forward primer; Primer code: I

<400> SEQUENCE: 8
attcttcggc ctgagtaact g                                        21

<210> SEQ ID NO 9
<211> LENGTH: 17
<212> TYPE: DNA
<213> ORGANISM: Artificial Sequence
<220> FEATURE:
<223> OTHER INFORMATION: Forward primer; Primer code: K

<400> SEQUENCE: 9
accctgcttc ggtgtcg                                             17

<210> SEQ ID NO 10
<211> LENGTH: 20
<212> TYPE: DNA
<213> ORGANISM: Artificial Sequence
<220> FEATURE:
<223> OTHER INFORMATION: Forward primer; Primer code: P

<400> SEQUENCE: 10
tcagaaatac caacgagagc                                          20

<210> SEQ ID NO 11
<211> LENGTH: 20
<212> TYPE: DNA
<213> ORGANISM: Artificial Sequence
<220> FEATURE:
<223> OTHER INFORMATION: Forward primer; Primer code: R

<400> SEQUENCE: 11
acatctcgtt ctcggtttat                                          20

<210> SEQ ID NO 12
<211> LENGTH: 21
<212> TYPE: DNA
<213> ORGANISM: Artificial Sequence
<220> FEATURE:
<223> OTHER INFORMATION: Forward primer; Primer code: T

<400> SEQUENCE: 12
attatcacta gtaggagagc a                                        21

<210> SEQ ID NO 13
<211> LENGTH: 20
<212> TYPE: DNA

```
<213> ORGANISM: Artificial Sequence
<220> FEATURE:
<223> OTHER INFORMATION: Forward primer; Primer code: W

<400> SEQUENCE: 13
tccttcacca ggagcaaagg                                              20

<210> SEQ ID NO 14
<211> LENGTH: 20
<212> TYPE: DNA
<213> ORGANISM: Artificial Sequence
<220> FEATURE:
<223> OTHER INFORMATION: Forward primer; Primer code: Y

<400> SEQUENCE: 14
aggattgccc cactccaaaa                                              20

<210> SEQ ID NO 15
<211> LENGTH: 21
<212> TYPE: DNA
<213> ORGANISM: Artificial Sequence
<220> FEATURE:
<223> OTHER INFORMATION: Forward primer; Primer code: APF

<400> SEQUENCE: 15
gaatcacagt atacgctcca t                                            21

<210> SEQ ID NO 16
<211> LENGTH: 19
<212> TYPE: DNA
<213> ORGANISM: Artificial Sequence
<220> FEATURE:
<223> OTHER INFORMATION: Reverse primer: Primer code: D

<400> SEQUENCE: 16
gccagacgtg tgatttcca                                               19

<210> SEQ ID NO 17
<211> LENGTH: 21
<212> TYPE: DNA
<213> ORGANISM: Artificial Sequence
<220> FEATURE:
<223> OTHER INFORMATION: Reverse primer: Primer code: H

<400> SEQUENCE: 17
gtcactccat ccactgtctc c                                            21

<210> SEQ ID NO 18
<211> LENGTH: 22
<212> TYPE: DNA
<213> ORGANISM: Artificial Sequence
<220> FEATURE:
<223> OTHER INFORMATION: Reverse primer: Primer code: J

<400> SEQUENCE: 18
gtcatttctg tctctaggct cc                                           22

<210> SEQ ID NO 19
<211> LENGTH: 18
<212> TYPE: DNA
<213> ORGANISM: Artificial Sequence
<220> FEATURE:
<223> OTHER INFORMATION: Reverse primer: Primer code: L

<400> SEQUENCE: 19
agccttcctg cctggtaa                                                18
```

-continued

<210> SEQ ID NO 20
<211> LENGTH: 22
<212> TYPE: DNA
<213> ORGANISM: Artificial Sequence
<220> FEATURE:
<223> OTHER INFORMATION: Reverse primer: Primer code: M

<400> SEQUENCE: 20
cattctttcc tggtctcact cc                                           22

<210> SEQ ID NO 21
<211> LENGTH: 23
<212> TYPE: DNA
<213> ORGANISM: Artificial Sequence
<220> FEATURE:
<223> OTHER INFORMATION: Reverse primer: Primer code: N

<400> SEQUENCE: 21
gactttcctt ttccacgacc atc                                          23

<210> SEQ ID NO 22
<211> LENGTH: 20
<212> TYPE: DNA
<213> ORGANISM: Artificial Sequence
<220> FEATURE:
<223> OTHER INFORMATION: Reverse primer: Primer code: O

<400> SEQUENCE: 22
gctctgccaa ttgactttcc                                              20

<210> SEQ ID NO 23
<211> LENGTH: 20
<212> TYPE: DNA
<213> ORGANISM: Artificial Sequence
<220> FEATURE:
<223> OTHER INFORMATION: Reverse primer: Primer code: Q

<400> SEQUENCE: 23
gagcaggtaa atgtcagtca                                              20

<210> SEQ ID NO 24
<211> LENGTH: 21
<212> TYPE: DNA
<213> ORGANISM: Artificial Sequence
<220> FEATURE:
<223> OTHER INFORMATION: Reverse primer: Primer code: U

<400> SEQUENCE: 24
tatttctgat aaaccgagaa c                                            21

<210> SEQ ID NO 25
<211> LENGTH: 20
<212> TYPE: DNA
<213> ORGANISM: Artificial Sequence
<220> FEATURE:
<223> OTHER INFORMATION: Reverse primer: Primer code: V

<400> SEQUENCE: 25
ggtaaatgtc agtcaagcac                                              20

<210> SEQ ID NO 26
<211> LENGTH: 20
<212> TYPE: DNA
<213> ORGANISM: Artificial Sequence
<220> FEATURE:

```
<223> OTHER INFORMATION: Reverse primer: Primer code: X

<400> SEQUENCE: 26
tgcctggtaa cgtagacacc                                              20

<210> SEQ ID NO 27
<211> LENGTH: 20
<212> TYPE: DNA
<213> ORGANISM: Artificial Sequence
<220> FEATURE:
<223> OTHER INFORMATION: Reverse primer: Primer code: Z

<400> SEQUENCE: 27
cctgcctggt aacgtagaca                                              20

<210> SEQ ID NO 28
<211> LENGTH: 20
<212> TYPE: DNA
<213> ORGANISM: Artificial Sequence
<220> FEATURE:
<223> OTHER INFORMATION: Reverse primer: Primer code: APR

<400> SEQUENCE: 28
cattcttaac ttggctcgac                                              20
```

METHOD AND KIT FOR CCR2 EXPRESSION PROFILING AND DISEASE STRATIFICATION

RELATED APPLICATION

This application claims the benefit of U.S. Provisional Application No. 63/054,407, filed on Jul. 21, 2020. The entire teachings of the above application are incorporated herein by reference.

INCORPORATION BY REFERENCE OF MATERIAL IN ASCII TEXT FILE

This application incorporates by reference the Sequence Listing contained in the following ASCII text file being submitted concurrently herewith:
 a) File name: 54311005004_SEQUENCELISTING.txt; created Jul. 21, 2021, 27 KB in size.

BACKGROUND

In assessing pharmacological intervention, a patient population can have a diverse biological makeup, which can impact the pharmacokinetic and pharmacodynamics response to the pharmacological intervention. For example, patients have unique genomes, gene expression profiles, and proteomic profiles, which can influence patient responses to pharmacological treatment.

SUMMARY

Methods and kits described herein are useful in assessing and stratifying a patient population. Properly stratified using relevant biomarkers, patient populations or subpopulations can be identified that are more responsive to a pharmacological agent. In particular, methods and kits described herein are useful in stratifying a patient population with respect to responsiveness to C-C chemokine receptor type 2 (CCR2) antagonists.

Described herein is a method for treating a disease in a patient in need thereof. The method can include measuring a CCR2 profile of the patient, selecting a compound based on the CCR2 profile of the patient, and administering the CCR2 antagonist to the patient. The compound can be a CCR2 antagonist, agonist, or mixed agonist. The CCR2 profile can include a profile of CCR2 isoform A, CCR2 isoform B, or both. Each CCR2 isoform can include one or more respective polymorphisms. The compound can be an antagonist or agonist of at least one polymorphism identified from the measured CCR2 profile of the patient.

Measuring the CCR2 profile can include sequencing CCR2 proteins or nucleic acids within the patient. Measuring the CCR2 profile can include sequencing nucleic acids within the patient. The nucleic acids can be DNA. The nucleic acids can be mRNA, such as mRNA within a bodily fluid (e.g., blood) of the patient. The method can further include separating a biological material based on the sequenced proteins or nucleic acids. The biological material can include cells, tissue, blood, other bodily fluids, or a combination thereof.

Measuring the CCR2 profile of the patient can include measuring a CCR2 profile of one or any combination of the patient's cells, the patient's tissues, the patient's blood, other bodily fluids of the patient. Measuring the CCR2 profile of the patient can include measuring a CCR2 profile of the patient's cells, optionally wherein the cells are a plurality of cell types. Measuring the CCR2 profile of the patient of the patient can include measuring a CCR2 profile of the patient's tissues, optionally wherein the tissues are a plurality of tissue types. Measuring the CCR2 profile of the patient can include measuring a CCR2 profile of the patient's other bodily fluids, optionally wherein the other bodily fluids are a plurality of types of bodily fluids. Measuring the CCR2 profile of the patient can include measuring a protein expression level for CCR2 isoform A, CCR2 isoform B, or both. The method can further include separating a biological material based on the measured protein expression level for CCR2 isoform A, CCR2 isoform B, or both. The biological material can include cells, tissue, blood, other bodily fluids, or a combination thereof.

Measuring a CCR2 profile can include subjecting a biological material to one or more compounds. The biological material can include cells, tissue, blood, other bodily fluids, or a combination thereof. The one or more compounds can be antagonists or agonists of at least one polymorphism identified from the measured CCR2 profile of the patient. The method can further include measuring one or more of biochemical, molecular biological, and cellular biological changes in the biological material prior to and after subjecting the biological material to the one or more compounds. Measuring a CCR2 profile can include obtaining a biological sample from the patient.

The compound can be one or more of INCB-8761/PF-4136309, MK-0812, BMS-813160, INCB-003284, PF-04634817, BMS-741672, Cenicriviroc (CCR2+CCR5), and CCX-140. Also described is a kit for performing any of such methods, where the kit can include one or more reagents for measuring a CCR2 profile of the patient.

The selected compound can be an antagonist of at least one polymorphism of CCR2 isoform A identified from the measured CCR2 profile of the patient. The selected compound can be an agonist of at least one polymorphism of CCR2 isoform A identified from the measured CCR2 profile of the patient. The selected compound can be an antagonist of at least one polymorphism of CCR2 isoform B identified from the measured CCR2 profile of the patient. The selected compound can be an agonist of at least one polymorphism of CCR2 isoform B identified from the measured CCR2 profile of the patient. The selected compound can be one of either an antagonist or an agonist for each of a plurality of polymorphisms of CCR2 isoform A identified from the measured CCR2 profile of the patient. The selected compound can be an antagonist for each of a plurality of polymorphisms of CCR2 isoform A identified from the measured CCR2 profile of the patient. The selected compound can be an agonist for each of a plurality of polymorphisms of CCR2 isoform A identified from the measured CCR2 profile of the patient. The selected compound can be one of either an antagonist or agonist for each of a plurality of polymorphisms of CCR2 isoform B identified from the measured CCR2 profile of the patient. The selected compound can be an antagonist for each of a plurality of polymorphisms of CCR2 isoform B identified from the measured CCR2 profile of the patient. The selected compound can be an agonist for each of a plurality of polymorphisms of CCR2 isoform B identified from the measured CCR2 profile of the patient. The selected compound can be an agonist of at least one polymorphism of CCR2 isoform A identified from the measured CCR2 profile of the patient and an antagonist of at least one polymorphism of CCR2 isoform B identified from the measured CCR2 profile of the patient. The selected compound can be an antagonist of at least one polymorphism of CCR2 isoform A identified from the measured CCR2 profile of the patient and an agonist of at least one polymorphism of CCR2 isoform B identified from the measured CCR2 profile of the patient.

Described herein is a method for stratifying one or more patients for pain medication based on a CCR2 profile. The method can include measuring a CCR2 profile of one or more patients and partitioning the one or more patients into predetermined groups or subgroups based on the CCR2 profile of the one or more patients. The CCR2 profile can include a profile of CCR2 isoform A, CCR2 isoform B, or both. Each CCR2 isoform can include one or more respective polymorphism.

Measuring the CCR2 profile of the one or more patients can include sequencing CCR2 proteins or nucleic acids within the patient. The nucleic acids can be DNA. The nucleic acids can be mRNA, such as mRNA within a bodily fluid (e.g., blood) of the patient. The method can further include separating a biological material based on the sequenced proteins or nucleic acids. The biological material can include cells, tissue, blood, other bodily fluids, or a combination thereof.

Measuring the CCR2 profile of the one or more patients can include measuring a CCR2 profile of one or any combination of the patient's cells, the patient's tissues, the patient's blood, and other bodily fluids of the patient. Measuring the CCR2 profile of the one or more patients can include measuring a CCR2 profile of the patient's cells, optionally wherein the cells are a plurality of cell types. Measuring the CCR2 profile of the one or more patients can include measuring a CCR2 profile of the patient's tissues, optionally wherein the tissues are a plurality of tissue types. Measuring the CCR2 profile of the one or more patients can include measuring a CCR2 profile of the patient's other bodily fluids, optionally wherein the other bodily fluids are a plurality of types of bodily fluids. Measuring the CCR2 profile of the one or more patients can include measuring protein expression level for CCR2 isoform A, CCR2 isoform B, or both. The method can further include separating a biological material based on the measured protein expression level for CCR2 isoform A, CCR2 isoform B, or both.

Measuring a CCR2 profile can include subjecting a biological material to one or more compounds. The biological material can include cells, tissue, blood, other bodily fluids, or a combination thereof. The one or more compounds can be antagonists or agonists of at least one polymorphism of identified from the measured CCR2 profile of the patient. The method can further include measuring one or more of biochemical, molecular biological, and cellular biological changes in the biological material prior to and after subjecting the cells to the one or more compounds. Measuring a CCR2 profile can include obtaining a biological sample from the patient.

The CCR2 one or more compounds can be one or more of INCB-8761/PF-4136309, MK-0812, BMS-813160, INCB-003284, PF-04634817, BMS-741672, Cenicriviroc (CCR2+ CCR5), and CCX-140.

The method can further include identifying statistically significant differences among patient groups or subgroups. Also described is a kit for performing any of such methods, where the kit can include one or more reagents for measuring a CCR2 profile of the patient. The CCR2 profile can include a profile of CCR2 isoform A, CCR2 isoform B, or both. Each CCR2 isoform can include one or more respective polymorphisms. The one or more reagents comprises a forward primer comprising a sequence selected from SEQ ID NOs: 7 through 15 and a reverse primer comprising a sequence selected from SEQ ID NOs: 16 through 28.

Described herein is a method for generating a profile of CCR2A and CCR2B isoform expression levels for a human subject. The method includes: a) obtaining a sample from the human subject; b) extracting RNA from the sample; c) performing reverse transcription on the extracted RNA to generate cDNA; d) amplifying the cDNA by performing polymerase chain reaction (PCR) by using a forward primer comprising a sequence selected from SEQ ID NOs: 7 through 15 and a reverse primer comprising a sequence selected from SEQ ID NOs: 16 through 28; and e) quantifying CCR2A and CCR2B isoform expression levels from the amplified cDNA.

Quantifying CCR2A and CCR2B isoform expression levels can be performed in a variety of ways, including by gel densitometry, blotting, nucleic acid hybridization, fluorescent in situ hybridization, reverse transcription-polymerase chain reaction, real-time polymerase chain reaction, microarray, nucleic acid sequencing, enzyme-linked immunosorbent assay (ELISA), colorimetric quantification, or other optical methods.

The sample can be blood. The sample can be a bodily secretion, such as saliva, urine, nasal mucosa, or vaginal mucosa.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 1 is a human CCR2 isoform A (SEQ ID NO: 3) vs. B (SEQ ID NO: 6) protein sequence comparison.

FIG. 2 is a human CCR2 isoform A (SEQ ID NO: 1) vs. B (SEQ ID NO: 4) cDNA sequence comparison.

FIG. 5 is a chart of CCR2 polymorphisms identified by rs number.

FIG. 7A is the CCR2A/2B ratio of three human subjects with diabetes. FIG. 7B is the CCR2A/2B ratio of eight human subjects with diabetic neuropathy. FIG. 7C is the CCR2A/2B ratio of six normal human subjects without diabetes-related disease.

DETAILED DESCRIPTION

Figure 3:
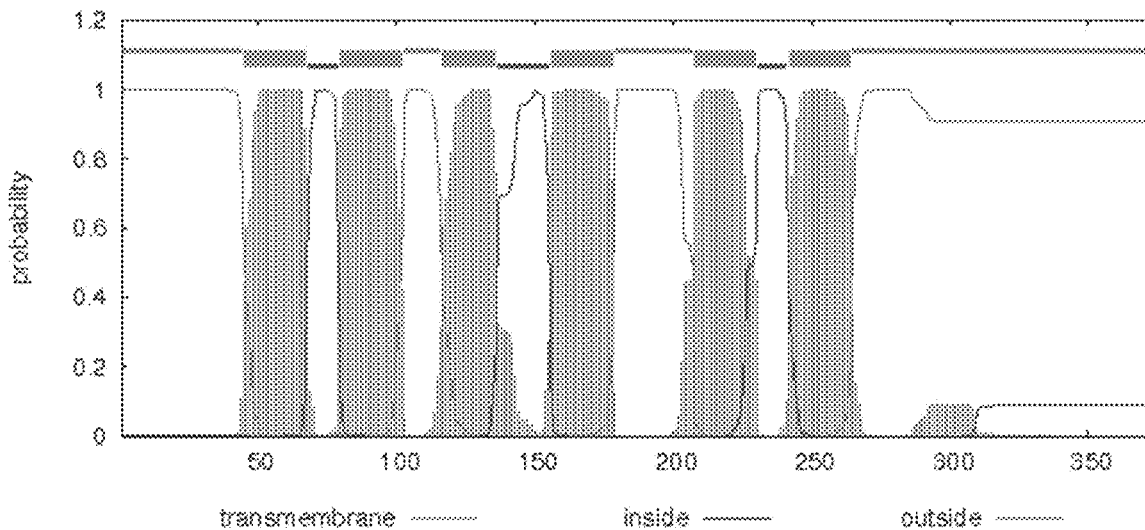
FIG. 3 is a graph of human CCR2 isoform A transmembrane helices.

A description of example embodiments follows.

As used herein, an "agonist" is an agent (e.g., compound) that binds to a receptor and activates the receptor to produce a biological response, such as an increase or decrease in expression or activity of a target gene, protein, or a pathway. An agonist can also increase the activity of a pathway through modulating the activity of pathway components, for example, through inhibiting the activity of negative regulators of a pathway. For example, an agonist of CCR2 isoform A is an agent that binds to the C-C chemokine receptor type 2 isoform A. An agonist of CCR5 is an agent that binds to the C-C chemokine receptor type 5. As used herein, an "agonist" encompasses an "inverse agonist," which is an agent (e.g., a compound) that binds to the same receptor as a reference agonist, but induces an opposite biological response relative to the reference agonist. As used herein, an "agonist" encompasses a "partial agonist," which is an agent (e.g., a compound) that binds to the same receptor as a reference agonist, but produces a biological response having only partial efficacy relative to the reference agonist. As used herein, an "agonist" encompasses a "partial inverse agonist," which is an agent (e.g., a compound) that binds to the same receptor as a reference agonist, but induces an opposite biological response relative to the reference agonist and having only partial efficacy relative to a reference inverse agonist. As used herein, an "antagonist" is an agent (e.g., compound) that binds to a receptor and dampens a biological response by binding to and blocking a receptor rather than activating it like an agonist. As used herein, an "antagonist" encompasses a "partial antagonist," which is an agent (e.g., a compound) that binds to a receptor and partially dampens a biological response. Whether a compound is an agonist, an inverse agonist, a partial agonist, a partial inverse agonist, or an antagonist can be measured by methodologies to detect molecular interactions such as proximity determination analysis. In another example of embodiment, cellular activities at the biochemical and/or physiological levels are determined as a measure of an agent's agonist activity, either in single cells, or in cell-cell interactions, or both. In yet another example of embodiment, a chemical indicator or indicators, such as fluorescent indicator compounds and/or luciferase markers, are introduced into an assay, and an agent's agonist activity is determined by measuring the said chemical indicators' properties. In yet another example of embodiment, one or more chemical indicators, one or more cellular types, or a mixture of chemical indicators and cellular types, are placed on a containment, said containment consisting of paper, cloth, plastic or other forms of polymers, metal, or a combination thereof; then an agent and said containment are enabled to be in contact, and an agent's agonist activity is determined by measuring the said chemical indicators' properties and/or cellular activities. In yet another example of embodiment, an agonist to be measured is in a purified form, or in a mixture of liquid, solid, and/or gas state, and is enabled to be in contact with a containment described above, for the purpose of measuring an agonist's activity.

Whether a compound is an agonist or antagonist, and the degree of agonism or antagonism, can be determined and measured by methodologies that detect molecular interactions such as proximity determination analysis. In another example embodiment, cellular activities at the biochemical and/or physiological levels are determined as a measure of an agent's agonist activity, either in single cells, or in cell-cell interactions, or both. In yet another example embodiment, a chemical indicator or indicators, such as fluorescent indicator compounds and/or luciferase markers, are introduced into an assay, and an agent's agonist activity is determined by measuring the said chemical indicators' properties. In yet another example embodiment, one or more chemical indicators, one or more cellular types, or a mixture of chemical indicators and cellular types, are placed on a containment, said containment consisting of paper, cloth, plastic or other forms of polymers, metal, or a combination thereof; then an agent and said containment are enabled to be in contact, and an agent's agonist activity is determined by measuring the said chemical indicators' properties and/or cellular activities. In yet another example embodiment, an agonist to be measured is in a purified form, or in a mixture of liquid, solid, and/or gas state, and is enabled to be in contact with a containment described above, for the purpose of measuring an agonist's activity.

In some instances, a compound can be an agonist of a CCR2 isoform and also an antagonist of another CCR2 isoform, and vice-versa. In some instances, a compound can be an agonist of a CCR2 isoform and also an antagonist of another CCR type, such as CCR5. Compounds exhibiting any of these characteristics can be referred to as a "mixed agonist-antagonist" or a "mixed antagonist-agonist."

Genetic variations exist in human beings, making each human being unique at the genetic level. Even for identical twins, the exact gene activity levels are different. Pharmaceutical compounds, when utilized to treat certain pathological conditions, produce varied treatment results in different individuals. A contributing factor to such inter-individual responses to drug treatment is likely genetic differences among individuals.

Described herein are methods and kits for use in stratifying members of a population (e.g., member of a patient population, preferably a human patient population) based on their specific genetic profiles of a given biological system, particularly the C-C chemokine receptor 2 (CCR2). Stratifying a patient population can be useful in a variety of clinical studies, including, without limitation, in prospective and retrospective cohort studies. For example, it can be desirable to study an association between an outcome variable (e.g., a clinical endpoint, such as degree of pain remission) and an exposure variable (e.g., treatment with a given dose of a given CCR2 receptor antagonist). In such a study, the strength of correlation between the exposure variable and the outcome variable can be masked, changed, altered, or confounded by relevant, though unaccounted-for, CCR system heterogeneities among patients. Stratifying a patient population (e.g., according to relevant CCR system markers, characteristics, genotypes, or phenotypes) prior to statistical analysis could aid in refining these relationships, and therefore in conducting clinical studies. Some CCR2 antagonists are likely to be more or less effective than others for individuals in different CCR2 strata. This could in turn improve drug treatment outcomes, as drugs could be administrated to patients with specific genetic profiles, based on knowledge of the relationship between that genetic type and efficacy of treatment with a given CCR2 antagonist.

The C-C chemokine receptor (CCR) system is highly complex and has been studied in academia and industry in efforts to elucidate the role of individual components in many distinct diseases marked by underlying inflammation. Some of these diseases include multiple sclerosis, rheumatoid arthritis, osteoarthritis, chronic obstructive pulmonary disease, chronic pain, and others. However, the CCR biology is insufficiently understood to enable successful clinical interventions. The methods and kits described herein address a large gap in the scientific understanding of the CCR system based on a detailed understanding of the genetic and expression variability among patients and disease states. As a result, more successful clinical development strategies can be formulated. The chemokine network is known to have at least 20 receptors and 80 ligands and displays promiscuity. CCR2 (aka CD192) may bind CCL2 (MCP1), CCL7 (MCP3), CCL8 (MCP2), CCL13 (MCP4), and CCL16.

The C-C chemokine receptor type 2 (CCR2) protein is encoded by the CCR2 gene. CCR2 is a member of a large family of inflammatory mediators and there is considerable pre-clinical evidence of its role in contributing to pain. Several knock out (KO) mice studies and in vivo models (e.g., chronic constriction injury (CCI) and spinal nerve ligation) demonstrated the role of CCR2 in pain.

Figure 4:
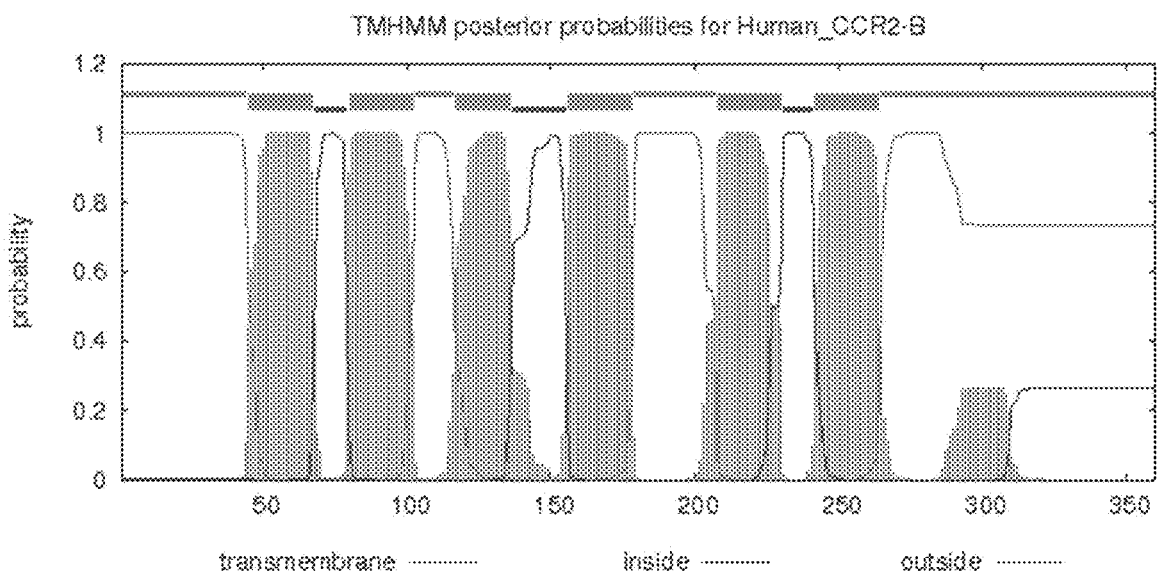
FIG. 4 is a graph of human CCR2 isoform B transmembrane helices.
Figure 6:
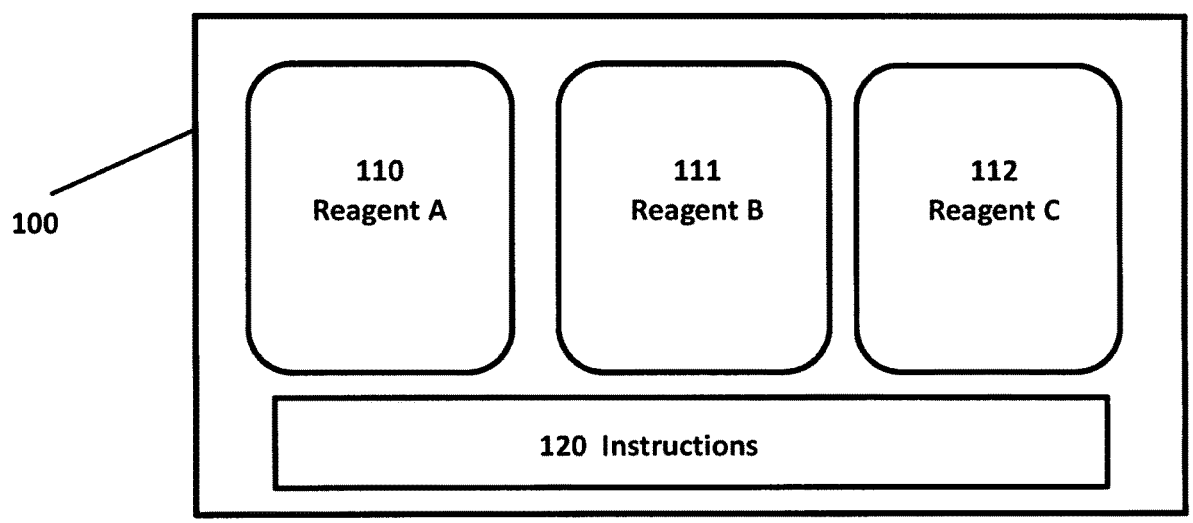
FIG. 6 is an illustration of a kit for performing methods described herein.

CCR2 exhibits substantial differences at the genetic and protein level. At least two alternatively spliced transcript variants are known to exist. As shown in the CCR2 isoform A vs. B protein (FIG. 1) and mRNA (FIG. 2) sequence comparisons, a major portion of CCR2 isoforms A and B is identical, starting at the 5' end of the CCR2 mRNA, and at the amino terminus of the CCR2 protein. However, sequence divergence is striking closer to the carboxyl terminus portion of the CCR2 protein (corresponding to the 3' portion of the CCR2 mRNA), with little sequence homology at either the protein level or the mRNA level. In addition, over 1,200 polymorphisms have been reported for the CCR2 gene region. FIG. 2 is the primary sequence information for the two isoforms, highlighting the specific differences in the receptor A and B isoforms at the genetic level. FIGS. 3 and 4 are hydrophobicity plots for CCR2A and CCR2B, respectively, showing the predicted transmembrane regions of the receptors and illustrating the differences at the terminal ends that may confer some of the sequence-dependent functionalities of the receptors. FIG. 6 is a chart of CCR2 polymorphisms identified by rs number. The rs number refers to the reference single nucleotide polymorphism (SNP) ID number. These sequence diversities form the basis of CCR2 structural and functional variations.

CCR2 is also known to have A and B isoforms, and heterodimerization may occur. CCR2 may also heterodimerize with other C-C chemokine receptors (CCRs), such as CCR5. Additionally, different tissues display different expression profiles, which can also vary depending on levels of stress. A profile of these factors can represent a biochemical signature of an individual patient and provide indicia of anticipated response to CCR2 antagonists.

Patients diagnosed with different diseases may exhibit differences in CCR2 profiles. By evaluating CCR2 profiles, a patient population can be stratified based on genotype and phenotype. In general, stratification refers to partitioning a patient population into groups or subgroups based on particular genotypic or phenotypic markers. Stratification is based on assessing a combination of factors, including: 1) the specific genetic profile of CCR2 isoforms, A and/or B, as determined by the alternative splicing of expressed variants (A and/or B); 2) genomic variations within an individual's polymorphisms; 3) protein expression level (e.g., ng/mL or pg/mL) for each A and B isoform; 4) identity of the specific tissue expressing CCR2 A and/or B isoforms; and 5) changes in CCR2 protein expression and/or CCR2 mRNA expression from baseline under various forms of stress, such as acute and chronic injury and neuroinflammation, and in chronic diseases, such as diabetes, osteoarthritis, multiple sclerosis, rheumatoid arthritis, and diabetic neuropathy. Different population groups are expected to have different responses, some more favorable than others, to pharmacologic intervention with CCR2 antagonists, agonists, or mixed agonist-antagonists. For example, particular antagonists may show greater efficacy when administered to particular patient populations or subpopulations diagnosed with particular clinical indications, thereby providing improved methods of treatment. By stratifying a patient population based on appropriate factors and documenting individual patient profiles, clinical trials can be improved, for example, by providing CCR2 antagonists (or agonists or mixed agonist-antagonists) to particular patient groups or subgroups expected, or anticipated, to have improved response to one or more CCR2 antagonists (or agonists or mixed agonist-antagonists).

Examples of CCR2 antagonists include INCB-8761/PF-4136309, MK-0812, BMS-813160, INCB-003284, PF-04634817, BMS-741672, Cenicriviroc (CCR2+CCR5), and CCX-140.

INCB-8761 and PF-4136309 refer to a compound having the following structure:

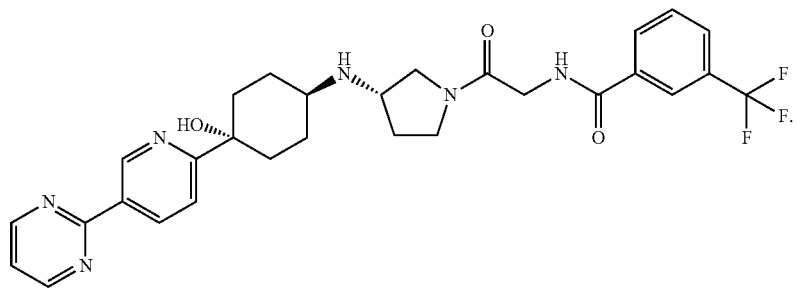 [SMILES: O=C(NCC(=O)N1CC[C@H](N[C@H]2CC[C@@](O)(c3ccc(-c4ncccn4)cn3)CC2)C1)c1cccc(C(F)(F)F)c1]

MK-0812 refers to a compound having the following structure:

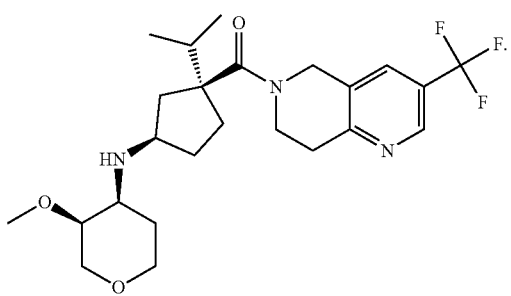 [SMILES: CO[C@@H]1COCC[C@@H]1N[C@@H]1CC[C@@](C(=O)N2CCc3ncc(C(F)(F)F)cc3C2)(C(C)C)C1]

BMS-813160 refers to a compound having the following structure:

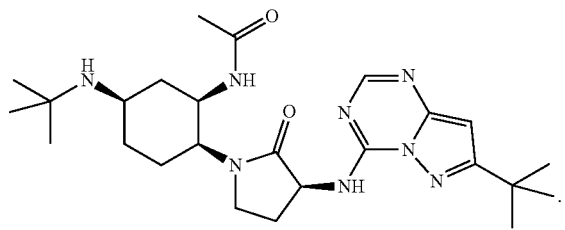 [SMILES: CC(=O)N[C@@H]1C[C@H](NC(C)(C)C)CC[C@@H]1N1CC[C@H](Nc2ncnc3cc(C(C)(C)C)nn23)C1=O]

INCB-003284 refers to a compound having the following structure:

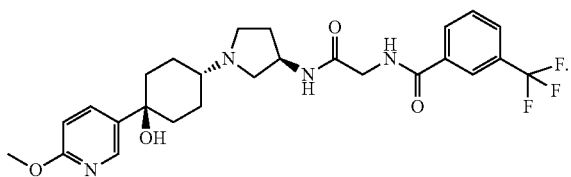 [SMILES: COc1ccc([C@]2(O)CC[C@H](N3CC[C@@H](NC(=O)CNC(=O)c4cccc(C(F)(F)F)c4)C3)CC2)cn1]

PF-04634817 refers to a compound having the following structure:

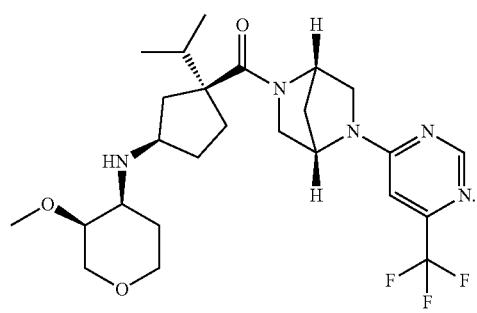 [SMILES: CO[C@@H]1COCC[C@@H]1N[C@@H]1CC[C@@](C(=O)N2C[C@@H]3C[C@H]2CN3c2cc(C(F)(F)F)ncn2)(C(C)C)C1]

BMS-741672 refers to a compound having the following structure:

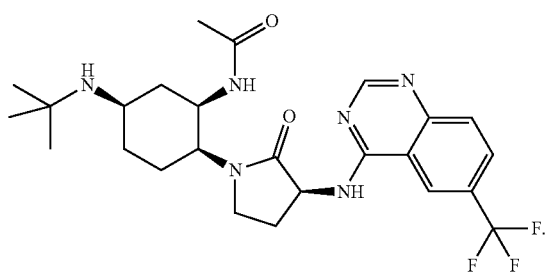 [SMILES: CC(=O)N[C@@H]1C[C@H](NC(C)(C)C)CC[C@@H]1N1CC[C@H](Nc2ncnc3ccc(C(F)(F)F)cc23)C1=O]

Cenicriviroc (CCR2+CCR5) refers to a compound having the following structure:

CCX-140 refers to a compound having the following structure:

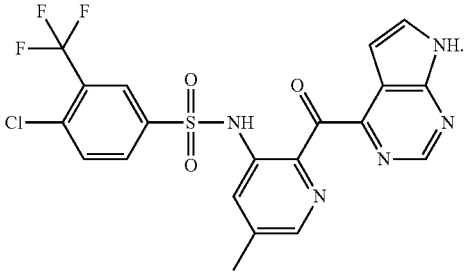

CCR2 antagonists, agonists, and mixed agonist-antagonists can be administered to patients suffering from pain associated with, or resulting from, a variety of diseases and disorders. Examples of particular diseases and disorders are described in WO 2010/071567 at pages 9-13, numbered paragraphs 1-15. The entire contents of pages 9-13, numbered paragraphs 1-15 of WO 2010/071567 is incorporated by reference herein in its entirety. Some examples of diseases and disorders for which pain can be treated by administration of a CCR2 antagonist include neuroinflammation and pain linked to CCR2. More particularly, pain can be associated with complex regional pain syndrome, neurofibromatosis, sarcoidosis, ankylosing spondylitis, postherpetic neuralgia, and painful diabetic neuropathy. In addition, pain can be associated with multiple sclerosis, rheumatoid arthritis, osteoarthritis, human immunodeficiency virus (HIV), and acquired immunodeficiency syndrome (AIDS).

The methods described herein utilize a genotyping approach to understand the genetic polymorphisms and gene expression profiles within a patient population to enable continued, and targeted, clinical development. Specifically, aspects of the invention relate to elucidating the molecular profile of CCR2 genotypes and isoforms, for determining the key pharmacological, biochemical, and stoichiometric parameters of the receptors, for assessing the acute and chronic desensitization of the receptors, and for measuring dosing and competition with ligand and test compound. The results will provide important clues to enable the design and implementation of clinical development strategies for targeting this important receptor.

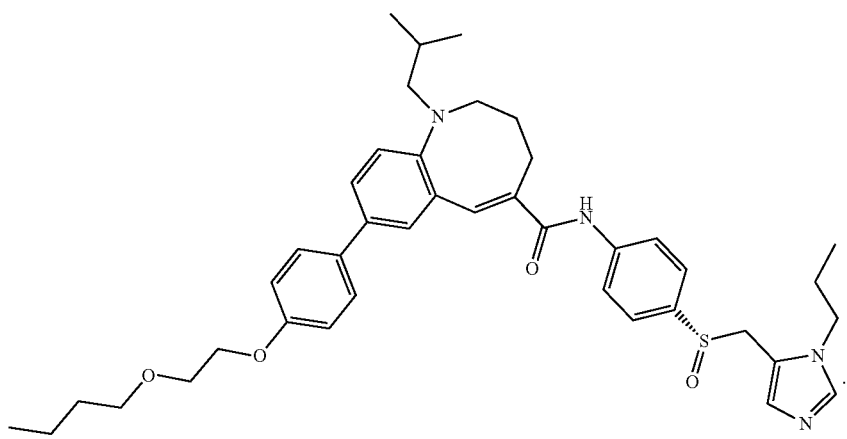 [SMILES: CCCCOCCOc1ccc(-c2ccc3c(c2)/C=C(/C(=O)Nc2ccc([S@@](=O)Cc4cncn4CCC)cc2)CCCN3CC(C)C)cc1]

Briefly, scientific validation involves the following steps, which are described in more detail in subsequent paragraphs: 1) Obtaining biological samples from a human patient population. Preferably, the biological samples have cells that express the CCR2 chemokine receptor. 2) Measuring CCR2 genotype variations (polymorphisms) and expressed receptor mRNA diversity (receptor isoforms). 3) Separating cells based on said genotype polymorphisms and/or mRNA diversity; cells in this step may be either cells in said biological samples, or cells containing said polymorphisms/mRNA diversity that are constructed using molecular genetics techniques. 4) Subjecting said cells to one or more chemical compounds that display CCR2 affinity, such as CCR2 antagonists, agonists, or mixed agonist-antagonists. 5) Measuring biochemical, molecular biological, and/or cellular biological changes in said cells both without and with said chemical compound exposure. 6) Performing analysis to determine if said changes represent statistically significant differences; statistically significant differences from such analysis validate the method for patient stratification, at a pre-clinical therapeutic intervention level.

Measuring CCR2 genotype variations (polymorphisms) can include sequencing nucleic acids (e.g., DNA and/or RNA) from individual's biological material (e.g., cells, tissue, blood, other bodily fluids, or a combination thereof), subjecting the nucleic acids to pre-formed templates such as microarray chips to quantify the extent and the nature of genotype variations, and deducing genotype variations by a variety of molecular detection methods such as mass spectrometry/spectroscopy, electrophoresis, and marker-mediated sorting.

Measuring expressed receptor mRNA diversity can include sequencing mRNA from an individual's biological material (e.g., cells, tissue, blood, other bodily fluids, or a combination thereof), either directly or by first converting said mRNA into cDNA form, subjecting mRNA to pre-formed templates such as microarray chips to quantify the extent and the nature of mRNA diversity, and deducing mRNA diversity by a variety of molecular detection methods such as mass spectrometry/spectroscopy, electrophoresis, and marker-mediated sorting. In some instances, mRNA is obtained from a blood sample of a patient.

Separating cells based on said genotype polymorphisms and/or mRNA diversity can include cell staining, marker-mediated sorting, density differentiation, morphology differentiation, biochemical differentiation, and functional differentiation.

Subjecting said biological material (e.g., cells, tissue, blood, other bodily fluids, or a combination thereof) to one or more chemical compounds that display CCR2 affinity can include direct exposure of cells to said chemical compounds in a variety of milieu, or indirect exposure of cells to said chemical compounds by placing cells in conditions where said chemical compounds have been a component thereof.

Measuring biochemical, molecular biological, and/or cellular biological changes in said biological material (e.g., cells, tissue, blood, other bodily fluids, or a combination thereof) both without and with said chemical compound exposure can include exposing said biological material to a variety of milieu containing said chemical compound or another compound serving as a comparison reference, then measuring desirable biochemical, molecular biological, and/or cellular biological changes in said cells either directly by physical, chemical, or other means, or indirectly by first obtaining certain cellular components from said biological material, then measuring biochemical, molecular biological, and/or cellular biological changes in said cellular components.

Other bodily fluids can include, for example, saliva, nasal mucus, sweat, cerebrospinal fluid, lymphoid fluid, vaginal secretion, rectal secretion, and urine.

Commercial validation can involve the following steps: A) Separating human patients into groups based on the above-described pre-clinical level stratification. B) Treating said human subject groups with CCR2 compounds (e.g., CCR2 agonists, antagonists, or mixed agonist-antagonists). C) Measuring biochemical, molecular biological, cellular biological, physiological, and/or behavioral changes in said human subjects. D) Performing an analysis to determine if said changes represent statistically significant differences among various human subject groups; statistically significant differences from such analysis can validate the method for patient stratification into clinical trials.

The methods described herein have a number of applications. For example, diagnostic kits or assays are provided that include appropriate reagents to enable users to apply the methods of patient stratification into clinical trials, and/or into medical treatment options. Said appropriate reagents can include nucleic acids, proteins, lipids, polysaccharides, inorganic compounds, organic compounds, cellular extracts, intact cell types, synthetic molecules, and combinations thereof. The methods can be utilized as a turn-key service for the purpose of better predicting the treatment outcome of a CCR2 receptor compound. These methods can be used for new pharmaceutical drug development. In one example embodiment, one or more diagnostic kits and/or assays are provided that include determining cellular activities at the biochemical and/or physiological levels, in single cells, in cell-cell interactions, and/or in cell-free environment. In another example embodiment, one or more diagnostic kits and/or assays are provided that include a chemical indicator or indicators, such as fluorescent indicator compounds and/or luciferase markers, and the said chemical indicators' properties are measured. In yet another example embodiment, one or more diagnostic kits and/or assays are provided that include one or more chemical indicators, one or more cellular types, or a mixture of chemical indicators and cellular types, said substances are placed on a containment that consists of paper, cloth, plastic or other forms of polymers, metal, or a combination thereof, and said containment is enabled to be in contact with samples to be tested, so that said chemical indicators' properties and/or cellular activities can be determined. In yet another example embodiment, one or more diagnostic kits and/or assays are provided that include samples to be tested in a purified form, or in a mixture of liquid, solid, and/or gas state, and said samples to be tested are enabled to be in contact with a containment described above, for the purpose of activity measurement.

FIG. 6 is an illustration of a kit 100 for performing methods described herein. The kit 100 includes one or more reagents for use in performing methods described herein. While FIG. 6 illustrates a kit 100 with three reagents (Reagent A 110, Reagent B 111, and Reagent C 112), a kit 100 can include more or fewer reagents, as appropriate. In some embodiments, kit 100 can also include instructions 120 for performing methods described herein.

One type of kit is for performing polymerase chain reaction (PCR) for selectively amplifying CCR2A or CCR2B. The kit includes forward and reverse primers for performing PCR.

In one embodiment, the forward primer comprises (or is) SEQ ID NO: 7. In one embodiment, the forward primer comprises (or is) SEQ ID NO: 8.

In one embodiment, the reverse primer comprises (or is) SEQ ID NO: 18. In one embodiment, the reverse primer comprises (or is) SEQ ID NO: 17. In one embodiment, the reverse primer comprises (or is) SEQ ID NO: 22.

In one embodiment, the forward primer comprises (or is) SEQ ID NO: 7, and the reverse primer comprises (or is) SEQ ID NO: 18. In one embodiment, the forward primer comprises (or is) SEQ ID NO: 8, and the reverse primer comprises (or is) SEQ ID NO: 18. In one embodiment, the forward primer comprises (or is) SEQ ID NO: 8, and the reverse primer comprises (or is) SEQ ID NO: 22. In one embodiment, the forward primer comprises (or is) SEQ ID NO: 7, and the reverse primer comprises (or is) SEQ ID NO: 17. In one embodiment, the forward primer comprises (or is) SEQ ID NO: 8, and the reverse primer comprises (or is) SEQ ID NO: 17.

Materials and Methods

Human Blood Samples

Human blood samples were used in the study, with seventeen study subjects as listed in Table 1

TABLE 1

Medical status of patients

| Medical Status | Age | Sex |
| --- | --- | --- |
| Diabetes | 49 | Male |
| Diabetes | 58 | Female |
| Diabetes | 62 | Male |
| Diabetic Neuropathy | 49 | Female |
| Diabetic Neuropathy | 52 | Female |
| Diabetic Neuropathy | 53 | Female |
| Diabetic Neuropathy | 60 | Male |
| Diabetic Neuropathy | 61 | Male |
| Diabetic Neuropathy | 61 | Male |
| Diabetic Neuropathy | 63 | Male |
| Diabetic Neuropathy | 77 | Female |
| Normal | 52 | Male |
| Normal | 54 | Male |
| Normal | 54 | Male |
| Normal | 55 | Female |
| Normal | 59 | Male |
| Normal | 68 | Female |

Total RNA was extracted from the 5 mL aliquots with the Monarch Total RNA Miniprep Kit (New England Biolabs) in conjunction with the Total RNA Purification from Mammalian Whole Blood Samples protocol provided by NEB (New England Biolabs). Extracted RNA samples were stored in aliquots at −80° C.

PCR

Designed PCR primers were ordered from Integrated DNA Technologies, Inc. Primer formulation is considered to be Lab Use Ready stock (100 μM). For each study subject RNA, reverse transcription was performed according to the protocol provided by ThermoFischer Scientific with their TaqMan Reverse Transcription Reagents kit. Each reverse transcription reaction produced 20 μl of cDNA that was then used for subsequent PCR reaction. PCR was performed using the Taq DNA Polymerase with Standard Taq Buffer PCR kit supplied by New England Biolabs. The New England Biolabs PCR protocol that accompanied the kit was used to perform PCR. Upon completion of PCR, agarose gel electrophoresis was performed, and the gel stained with ethidium bromide in order to visualize the PCR products.

Quantification of Splice Variant Expression Via Gel Densitometry

Gel densitometry was used to quantify isoform expression levels, performed with ImageJ, a Java-based image processing program. All CCR2 isoform PCR bands were compared against internal standard and/or GAPDH standard to allow for comparison across gel lanes. CCR2 isoform expression ratio was calculated based on the following equation: (CCR2B−CCR2A)/(CCR2B+CCR2A). The individual patient ratios were graphed and assessed qualitatively to determine whether the CCR2 isoform ratio changed across patients.

Results

Comparison of CCR2A Vs 2B Splice Variant Sequences

Prior to designing primers for CCR2A and CCR2B, we needed to understand the structure of the alternatively spliced variants. Research indicated that the protein sequences of the variants differed in their carboxyl terminals, which suggests that there is genetic sequence difference between the two splice variants. The nucleic acid sequence files for both human CCR2B and CCR2A were downloaded from NCBI website, and we performed sequence comparison. The sequence alignment depicted the regions where CCR2B and CCR2A overlapped.

Based on the sequence alignment, CCR2B contains an exon approximately around the middle section of the CCR2 nucleic acid sequence. Even though said exon results in a longer mRNA, differences in protein coding region results in CCR2A protein sequence longer than that for CCR2B.

Designing Common and Splice Variant-Specific PCR Primers

Once we had a clear understanding of the splice variant sequences for CCR2A and CCR2B, we designed PCR primers both for common regions of CCR2A and CCR2B, as well as splice variant-specific PCR primers that would isolate the specific variants. Developing PCR primers specific and optimal to each of the variants was a necessary step that would allow efficient variant isolation needed to quantify the individual expression levels of CCR2A and CCR2B in blood samples from a human subject. This would allow us to analyze expression levels in subjects to determine whether the CCR2 splice variant ratio differs among different people.

We used the NCBI primer design tool to produce multiple primers specific for either CCR2A or CCR2B, as well as common to both. Our parameters for primer design included: 1) primer length within 20-40 nucleotides; 2) GC content of 40-60%; and 3) melting temperature (Tm) between 45-68° C. Primers lengths were all approximately 20 base pairs long and had similar melting temperatures. We designed primers close to exon boundaries, so that variant specificity could be measured. Primers designed for CCR2B were located within the CCR2B-specific exon. We designed primers for CCR2A that theoretically could also isolate CCR2B, but because the extra exon in CCR2B was over 1,000 bases longer than CCR2A, its amplification would be very low quantity, relatively compared to that of CCR2A.

We used GAPDH as our internal control, so as to quantify the PCR amplification product.

Splice Variant Expression Levels

PCR products were analyzed by agarose gel electrophoresis, and the DNA bands were quantified by densitometry measurements using ImageJ software.

We used blood samples from normal healthy subjects, as well as diabetic patients with or without neuropathy. The results demonstrated that individual CCR2A/CCR2B ratios differ considerably among different study subjects, indicating that the CCR2 isoform ratios can serve as an indicator of a study subject's unique isoform levels, and that CCR2 isoform profiles can be used to stratify subject populations, for correlation with therapeutic treatment responders and non-responders.

Figure 7A:
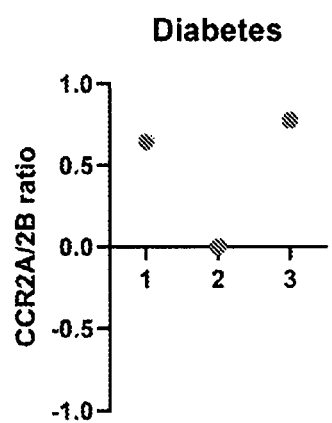
FIGS. 7A-C are graphs of ratios of human CCR2 isoforms in human subjects.
Figure 7B:
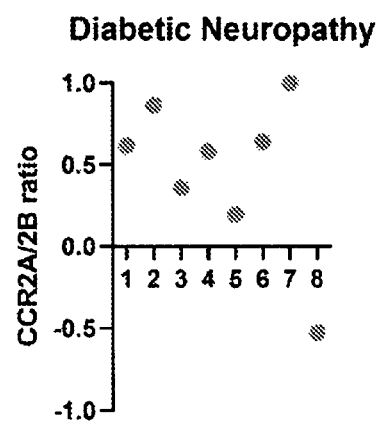
Figure 7C:
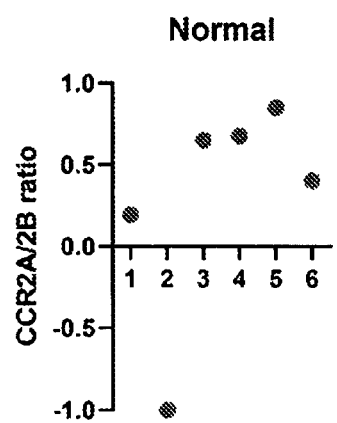

FIGS. 7A-C are graphs of ratios of human CCR2 isoform expression levels in human subjects, three with diabetes (FIG. 7A), eight with diabetic neuropathy (FIG. 7B), and six normal human subjects without diabetes-related disease (FIG. 7C).

PCR Primer Pair Efficiency

PCR primer pair efficiency: For each primer pair, the primer pair code and forward/reverse primer sequences are shown. Column 'CCR2A' indicates the expected PCR product length in base pairs. Column 'CCR2B' indicates the expected PCR product length in base pairs. When a primer pair is capable of amplifying both a smaller CCR2A product and a larger CCR2B product, the expected CCR2B product would be 1,208 base pairs longer than that of CCR2A, due to the additional exon sequence contained in CCR2B isoform. This makes the amplification of the larger CCR2B product inefficient, to the extent that the expected larger product is not observed. Thus, the larger band size of expected product is shown in parenthesis. Column 'Efficiency' shows percentage number of PCR amplification efficiency compared to the internal control, for the shorter product.

INDEX OF SEQUENCES

Table 2 provides an indexes of the sequences included with the sequence listing.

TABLE 2

| Index of sequence listing | |
|---|---|
| SEQ ID NO | Description |
| SEQ ID NO: 1 | CCR2 isoform A cDNA |
| SEQ ID NO: 2 | CCR2 isoform A mRNA |
| SEQ ID NO: 3 | CCR2 isoform A protein |
| SEQ ID NO: 4 | CCR2 isoform B cDNA |
| SEQ ID NO: 5 | CCR2 isoform B mRNA |
| SEQ ID NO: 6 | CCR2 isoform B protein |
| SEQ ID NO: 7 | Forward primer; Primer code: C |
| SEQ ID NO: 8 | Forward primer; Primer code: I |
| SEQ ID NO: 9 | Forward primer; Primer code: K |
| SEQ ID NO: 10 | Forward primer; Primer code: P |
| SEQ ID NO: 11 | Forward primer; Primer code: R |
| SEQ ID NO: 12 | Forward primer; Primer code: T |
| SEQ ID NO: 13 | Forward primer; Primer code: W |
| SEQ ID NO: 14 | Forward primer; Primer code: Y |
| SEQ ID NO: 15 | Forward primer; Primer code: APF |
| SEQ ID NO: 16 | Reverse primer: Primer code: D |
| SEQ ID NO: 17 | Reverse primer: Primer code: H |
| SEQ ID NO: 18 | Reverse primer: Primer code: J |
| SEQ ID NO: 19 | Reverse primer: Primer code: L |
| SEQ ID NO: 20 | Reverse primer: Primer code: M |
| SEQ ID NO: 21 | Reverse primer: Primer code: N |
| SEQ ID NO: 22 | Reverse primer: Primer code: O |
| SEQ ID NO: 23 | Reverse primer: Primer code: Q |
| SEQ ID NO: 24 | Reverse primer: Primer code: U |
| SEQ ID NO: 25 | Reverse primer: Primer code: V |
| SEQ ID NO: 26 | Reverse primer: Primer code: X |
| SEQ ID NO: 27 | Reverse primer: Primer code: Z |
| SEQ ID NO: 28 | Reverse primer: Primer code: APR |

INCORPORATION BY REFERENCE; EQUIVALENTS

The teachings of all patents, published applications and references cited herein are incorporated by reference in their entirety.

While example embodiments have been particularly shown and described, it will be understood by those skilled in the art that various changes, modifications, and enhance-

| Primer Pair Code | Forward Primer | Reverse Primer | CCR2A | CCR2B | Efficiency |
|---|---|---|---|---|---|
| CD | SEQ ID NO: 7 | SEQ ID NO: 16 | 453 | (1,661) | 22% |
| CH | SEQ ID NO: 7 | SEQ ID NO: 17 | — | 315 | 57% |
| CJ | SEQ ID NO: 7 | SEQ ID NO: 18 | 422 | (1,630) | 50% |
| CL | SEQ ID NO: 7 | SEQ ID NO: 19 | 513 | (1,721) | 13% |
| CM | SEQ ID NO: 7 | SEQ ID NO: 20 | 311 | (1,519) | 0% |
| CN | SEQ ID NO: 7 | SEQ ID NO: 21 | 360 | (1,568) | 15% |
| CO | SEQ ID NO: 7 | SEQ ID NO: 22 | 372 | (1,580) | 0% |
| ID | SEQ ID NO: 8 | SEQ ID NO: 16 | 360 | (1,568) | 25% |
| IH | SEQ ID NO: 8 | SEQ ID NO: 17 | — | 222 | 69% |
| IJ | SEQ ID NO: 8 | SEQ ID NO: 18 | 329 | (1,537) | 50% |
| IL | SEQ ID NO: 8 | SEQ ID NO: 19 | 420 | (1,628) | 22% |
| IM | SEQ ID NO: 8 | SEQ ID NO: 20 | 218 | (1,426) | 31% |
| IN | SEQ ID NO: 8 | SEQ ID NO: 21 | 267 | (1,475) | 27% |
| IO | SEQ ID NO: 8 | SEQ ID NO: 22 | 279 | (1,487) | 50% |
| KL | SEQ ID NO: 9 | SEQ ID NO: 19 | 548 | (1,756) | 0% |
| PQ | SEQ ID NO: 10 | SEQ ID NO: 23 | 218 | 218 | 46% |
| RV | SEQ ID NO: 11 | SEQ ID NO: 25 | 232 | 232 | 37% |

For selectively amplifying CCR2A, preferred primer pairs are CJ, IJ, and IO. For selectively amplifying CCR2B, preferred primer pairs are CH and IH.

ments in form and details may be made therein without departing from the scope of the embodiments encompassed by the appended claims.

What is claimed is:

1. A method for treating pain associated with diabetic neuropathy in a patient in need thereof, the method comprising:
   a) measuring expression levels of mRNA polymorphisms of CCR2A, CCR2B, or both of the patient;
   b) selecting a compound based on the measured mRNA polymorphisms of CCR2A, CCR2B, or both of the patient, wherein the selected compound is an antagonist of at least one polymorphism identified from the measured mRNA polymorphisms of CCR2A, CCR2B, or both of the patient;
   c) administering the selected compound to the patient.

2. A method for generating a profile of expression levels of mRNA polymorphisms of CCR2A, CCR2B, or both for a human subject with diabetic neuropathy, the method comprising:
   a) obtaining a sample from the human subject with diabetic neuropathy;
   b) extracting mRNA from the sample;
   c) performing reverse transcription on the extracted mRNA to generate cDNA;
   d) amplifying the cDNA by performing polymerase chain reaction (PCR) by using a forward primer comprising a sequence selected from SEQ ID NOs: 7 through 15 and a reverse primer comprising a sequence selected from SEQ ID NOs: 16 through 28; and
   e) quantifying expression levels of mRNA polymorphisms of CCR2A, CCR2B, or both from the amplified cDNA.

3. The method of claim 2, wherein the forward primer is SEQ ID NO: 7.

4. The method of claim 2, wherein the forward primer is SEQ ID NO: 8.

5. The method of claim 2, wherein the reverse primer is SEQ ID NO: 18.

6. The method of claim 2, wherein the reverse primer is SEQ ID NO: 17.

7. The method of claim 2, wherein the reverse primer is SEQ ID NO: 22.

8. The method of claim 2, wherein the forward primer is SEQ ID NO: 7, and wherein the reverse primer is SEQ ID NO: 18.

9. The method of claim 2, wherein the forward primer is SEQ ID NO: 8, and wherein the reverse primer is SEQ ID NO: 18.

10. The method of claim 2, wherein the forward primer is SEQ ID NO: 8, and wherein the reverse primer is SEQ ID NO: 22.

11. The method of claim 2, wherein the forward primer is SEQ ID NO: 7, and wherein the reverse primer is SEQ ID NO: 17.

12. The method of claim 2, wherein the forward primer is SEQ ID NO: 8, and wherein the reverse primer is SEQ ID NO: 17.

13. The method of claim 2, wherein quantifying expression levels of mRNA polymorphisms of CCR2A, CCR2B, or both is by gel densitometry, blotting, nucleic acid hybridization, fluorescent in situ hybridization, reverse transcription-polymerase chain reaction, real-time polymerase chain reaction, microarray, nucleic acid sequencing, enzyme-linked immunosorbent assay (ELISA), or colorimetric quantification.

14. The method of claim 2, wherein the sample is blood.

15. The method of claim 2, wherein the sample is a bodily secretion.

16. The method of claim 15, wherein the bodily secretion is saliva.

17. The method of claim 15, wherein the bodily secretion is urine.

18. The method of claim 15, wherein the bodily secretion is nasal mucosa.

19. The method of claim 15, wherein the bodily secretion is vaginal mucosa.

20. The method of claim 2, wherein the method is for treating the human subject with diabetic neuropathy, the method further comprising:

f) selecting a compound based on the measured mRNA polymorphisms of CCR2A, CCR2B, or both of the patient, wherein the selected compound is an antagonist of at least one polymorphism identified from the measured mRNA polymorphisms of CCR2A, CCR2B, or both of the patient; and g) administering the selected compound to the patient.

\* \* \* \* \*

UNITED STATES PATENT AND TRADEMARK OFFICE
CERTIFICATE OF CORRECTION

Page 1 of 1

PATENT NO. : 12,319,958 B2
APPLICATION NO. : 17/382240
DATED : June 3, 2025
INVENTOR(S) : Lei Yu and Thomas P. Richardson It is certified that error appears in the above-identified patent and that said Letters Patent is hereby corrected as shown below:

In the Claims

In Claim 1, Column 39, Line 30, delete "pain associated with"

Signed and Sealed this
Twenty-second Day of July, 2025

Coke Morgan Stewart
*Acting Director of the United States Patent and Trademark Office*